US009562249B2

(12) United States Patent
Klein et al.

(10) Patent No.: US 9,562,249 B2
(45) Date of Patent: *Feb. 7, 2017

(54) ACTINOMYCETE INTEGRATIVE AND CONJUGATIVE ELEMENT FROM *ACTINOPLANES* SP. SE50/110 AS PLASMID FOR GENETIC TRANSFORMATION OF RELATED ACTINOBACTERIA

(71) Applicant: Bayer Intellectual Property GmbH, Monheim (DE)

(72) Inventors: Andreas Klein, Nordkirchen (DE); Klaus Selber, Haan (DE); Hermann Wehlmann, Wuppertal (DE); Winfried Rosen, Remscheid (DE); Alfred Pühler, Bielefeld (DE); Patrick Schwientek, Davis, CA (US); Jörn Kalinowski, Bielefeld (DE); Udo Wehmeier, Wuppertal (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/939,495

(22) Filed: Nov. 12, 2015

(65) Prior Publication Data

US 2016/0130622 A1 May 12, 2016

Related U.S. Application Data

(63) Continuation of application No. 14/363,810, filed as application No. PCT/EP2012/074366 on Dec. 4, 2012, now Pat. No. 9,217,154.

(30) Foreign Application Priority Data

Dec. 8, 2011 (EP) .................... 11192618

(51) Int. Cl.
| C12N 15/52 | (2006.01) |
| C12P 19/26 | (2006.01) |
| C07K 14/365 | (2006.01) |
| C12P 19/28 | (2006.01) |
| C12N 15/76 | (2006.01) |
| C12N 15/74 | (2006.01) |

(52) U.S. Cl.
CPC .............. *C12P 19/26* (2013.01); *C07K 14/365* (2013.01); *C12N 15/52* (2013.01); *C12N 15/74* (2013.01); *C12N 15/76* (2013.01); *C12P 19/28* (2013.01)

(58) Field of Classification Search
None
See application file for complete search history.

(56) References Cited

U.S. PATENT DOCUMENTS

| 3,876,766 A | 4/1975 | Frommer et al. |
| 4,019,960 A | 4/1977 | Frommer et al. |
| 4,062,950 A | 12/1977 | Frommer |
| 2013/0302855 A1* | 11/2013 | Selber .................. C07K 14/365 435/84 |

FOREIGN PATENT DOCUMENTS

| WO | 2012/016960 A1 | 2/2012 |
| WO | 2013/083566 A1 | 6/2013 |

OTHER PUBLICATIONS

Ha et al., Biotechnol Lett, 2008, vol. 30, pp. 1233-1238.*
Burrus et al., "Shaping bacterial genomes with integrative and conjugative elements," Research in Microbiology, 2004, 155:376-386.
Caspary et al., "Inhibition of Human Intestinal a-Glucosidehydrolases by a New Complex Oligosaccharide," Res. Exp. Med. (Berl.), 1979, 175:1-6.
Frommer et al, "New Enzyme Inhibitors from Microorganisms," Journal of Medicinal Plant Research, Mar. 1979, 35 (3):195-217.
Grohmann et al., "Conjugative Plasmid Transfer in Gram-Positive Bacteria," Microbiology and Molecular Biology Reviews, Jun. 2003, 67(2):277-301.
Hagege et al., "Mode and origin of replication of pSAM2, a conjugative integrating element of Streptomyces ambofaciens," Molecular Microbiology, 1993, 10(4):799-812.
Heinzelmann et al., "A Glutamate Mutase Is Involved in the Biosynthesis of the Lipopeptide Antibiotic Friulimicin in Actinoplanes friuliensis," Antimicrobial Agents and Chemotherapy, Feb. 2003, 47(2):447-457.
Helmann, J. D., "The Extracytoplasmic Function (ECF) Sigma Factors," Advances in Microbial Physiology, 2002, 46:47-110.
Hosted et al., "Characterization of the Micromonospora rosaria pMR2 plasmid and development of a high G+C codon optimized integrase for site-speciWc integration," Plasmid, 2005, 54:249-258.
Wehmeier et al., "Biotechnology and molecular biology of the α-glucosidase inhibitor acarbose," Appl. Microbiol. Biotechnol., 2004, 63:613-625.
Kataoka et al. "Complete Nucleotide Sequence of the Streptomyces nigrifaciens Plasmid, pSN22: Genetic Organization and Correlation with Genetic Properties," Plasmid, 1994, 32:55-69.

(Continued)

*Primary Examiner* — Mindy G Brown
(74) *Attorney, Agent, or Firm* — Yonggang Ji

(57) ABSTRACT

The present invention is directed to an innate DNA sequence within the complete genome sequence of *Actinoplanes* sp. SE50/110 which resembles the structure of an actinomycete integrative and conjugative element (AICE). Related AICEs were used for establishing genetic manipulation tools for other bacteria in the past. In this document, we describe the unique features of the specific AICE found in *Actinoplanes* sp. SE50/110 which are clearly distinct from any other known AICE as a whole, but share minor parts with varying sequence similarity with other characterized AICEs from other species.

2 Claims, 2 Drawing Sheets

(56) References Cited

OTHER PUBLICATIONS

Possoz et al., "Conjugal immunity of Streptomyces strains carrying the integrative element pSAM2 is due to the oif gene (pSAM2 immunity factor)," Molecular Microbiology, 2003, 47(5):1385-1393.
Possoz et al., "The integrative element pSAM2 from Streptomyces: kinetics and mode of conjugal transfer," Molecular Microbiology, 2001-42(1):159-166.
Raynal et al., "Characterization of the attP site of the integrative element pSAM2 from Streptomyces ambofaciens," Microbiology, 2002, 148:61-67.
Reuther et al., "Unique conjugation mechanism in mycelial streptomycetes: a DNA-binding ATPase translocates unprocessed plasmid DNA at the hyphal tip," Molecular Microbiology, 2006, 61(2):436-446.
Schwientek et al., "The complete genome sequence of the acarbose producer *Actinoplanes* sp. SE50/110," BMC Genomics, 2012, 13(112):1-18.
Sezonov et al., "KorSA from the Streptomyces Integrative Element pSAM2 Is a Central Transcriptional Repressor: Target Genes and Binding Sites," Journal of Bacteriology, Mar. 2000, 182(5):1243-1250.
Te Poele et al., "Actinomycete integrative and conjugative elements," Antonie van Leeuwenhoek, 2008, 94:127-143.
Te Poele et al., "Actinomycete integrative and conjugative pMEA-like elements of Amycolatopsis and Saccharopolyspora decoded," Plasmid, 2008, 59:202-216.

\* cited by examiner

```
                       SEQUENCE LISTING

<160> NUMBER OF SEQ ID NOS: 46

<210> SEQ ID NO 1
<211> LENGTH: 13643
<212> TYPE: DNA
<213> ORGANISM: Actinoplanes sp. SE50/110
<220> FEATURE:
<221> NAME/KEY: gene
<222> LOCATION: (112)..(1278)
<223> OTHER INFORMATION: gene name: int; coding strand: reverse
<220> FEATURE:
<221> NAME/KEY: gene
<222> LOCATION: (1275)..(1481)
<223> OTHER INFORMATION: gene name: xis; coding strand: reverse
<220> FEATURE:
<221> NAME/KEY: gene
<222> LOCATION: (1510)..(3306)
<223> OTHER INFORMATION: gene name: repSA; coding strand: reverse
<220> FEATURE:
<221> NAME/KEY: gene
<222> LOCATION: (3308)..(3601)
<223> OTHER INFORMATION: gene name: aice1; coding strand: reverse
<220> FEATURE:
<221> NAME/KEY: gene
<222> LOCATION: (3598)..(3921)
<223> OTHER INFORMATION: gene name: spdA; coding strand: reverse
<220> FEATURE:
<221> NAME/KEY: gene
<222> LOCATION: (3918)..(4427)
<223> OTHER INFORMATION: gene name: spdB; coding strand: reverse
<220> FEATURE:
<221> NAME/KEY: gene
<222> LOCATION: (4424)..(4714)
<223> OTHER INFORMATION: gene name: aice2; coding strand: reverse
<220> FEATURE:
<221> NAME/KEY: gene
<222> LOCATION: (4711)..(4896)
<223> OTHER INFORMATION: gene name: aice3; coding strand: reverse
<220> FEATURE:
<221> NAME/KEY: gene
<222> LOCATION: (4893)..(5309)
<223> OTHER INFORMATION: gene name: aice4; coding strand: reverse
<220> FEATURE:
<221> NAME/KEY: gene
<222> LOCATION: (5306)..(5632)
<223> OTHER INFORMATION: gene name: aice5; coding strand: reverse
<220> FEATURE:
<221> NAME/KEY: gene
<222> LOCATION: (5629)..(6078)
<223> OTHER INFORMATION: gene name: aice6; coding strand: reverse
```

```
<220> FEATURE:
<221> NAME/KEY: gene
<222> LOCATION: (6165)..(6365)
<223> OTHER INFORMATION: gene name: aice7; coding strand: reverse
<220> FEATURE:
<221> NAME/KEY: gene
<222> LOCATION: (6362)..(7243)
<223> OTHER INFORMATION: gene name: tra; coding strand: reverse
<220> FEATURE:
<221> NAME/KEY: gene
<222> LOCATION: (7310)..(7684)
<223> OTHER INFORMATION: gene name: aice8; coding strand: reverse
<220> FEATURE:
<221> NAME/KEY: gene
<222> LOCATION: (7696)..(8616)
<223> OTHER INFORMATION: gene name: aice9; coding strand: reverse
<220> FEATURE:
<221> NAME/KEY: gene
<222> LOCATION: (8731)..(8940)
<223> OTHER INFORMATION: gene name: aice10; coding strand: reverse
<220> FEATURE:
<221> NAME/KEY: gene
<222> LOCATION: (9109)..(9426)
<223> OTHER INFORMATION: gene name: pra; coding strand: reverse
<220> FEATURE:
<221> NAME/KEY: gene
<222> LOCATION: (9663)..(10997)
<223> OTHER INFORMATION: gene name: reg; coding strand: forward
<220> FEATURE:
<221> NAME/KEY: gene
<222> LOCATION: (11012)..(11530)
<223> OTHER INFORMATION: gene name: nud; coding strand: forward
<220> FEATURE:
<221> NAME/KEY: gene
<222> LOCATION: (11542)..(11784)
<223> OTHER INFORMATION: gene name: mdp; coding strand: reverse
<220> FEATURE:
<221> NAME/KEY: gene
<222> LOCATION: (11881)..(12651)
<223> OTHER INFORMATION: gene name: aice11; coding strand: forward
<220> FEATURE:
<221> NAME/KEY: gene
<222> LOCATION: (12626)..(12907)
<223> OTHER INFORMATION: gene name: aice12; coding strand: reverse

<400> SEQUENCE: 1 ctggggtca  aggggtcgca  ggttcaaatc  ctgtcagccc  gacgcaggtc  agagggcata    60
tctcatcgaa  ggatatgccc  tctctgcatg  tctgggtaac  taactgggtg  actaagcccc   120
aggagtgtca  tccggaccga  agatccggtc  catggccacc  gcgccgttca  gcagaaccgg   180
gcgcagttgg  tggcggtaaa  cggtctcggt  gatcgaggtg  ccggaatgac  cacacaggtc   240
ggcgatttcc  tcgatgctca  tcccattgtc  ggacagcagc  gaaacgaaac  tgtgccgtaa   300
ttcgcggggc  gtccattcag  ccggattcat  tccggggaca  gccgcgacga  tcgcgcggaa   360
ggctcgcagc  acgttgtgcc  ggtcgagctg  ggtgccgacc  ttgctggcgc  agacgtagtc   420
atccggtcgt  ggatctccgt  gcgccgcgcg  ttgcgcggtg  aggacccgga  cacagcgaac   480
cggcagggcg  agtgaacgcc  gtgacttctt  ggtcttggtg  tcaccgtggg  cgcgcaccga   540
atgccatacg  tggatggccg  gcggaatcgg  tggctcggcg  tccggacgtc  cgaccaggtc   600
gacgtgctgc  caggtgagtt  ctcgcagttc  ctcggtacga  gcaccggtca  gcagcgacaa   660
aactacatac  gcgtgcaggc  tgctcgactc  ggcagcgacg  aggagcgctt  tggcctgctc   720
gtaggtgagt  gacttggagg  gtcgtccggc  ggtgccggtc  ggtaccttgc  agagtgcgac   780
gacgttgcgc  atgaccttgt  cgcgggccat  cgctcggttg  atggcgcgat  tcgcgatcga   840
gtgcagcagt  cgcagcgtgc  gggtgctgag  aatcttggct  ttgtcggcca  gccacctgtc   900
aatgtcggtg  gcgctgagtt  ccttctgttt  gctggggtca  cggagcttgc  gtgcaccgat   960
```

-continued

```
cgccgggatg atgtgaccgt tggccagcag cgtgtagttg ttgaccgttt cctcgtcgac    1020
gtcgggaagt ccgtaggtga gccagtccgt gacggcgtcg gcgaccgtgt agccggtcgt    1080
ggggatcgac agcccgtcct ggtactcacg gatcttctga cggagtgcat tgttggcctc    1140
ggtcttggtc ttgccgcttg ccttacggac gatgcgttta ccggccgggg tgtatccgac    1200
ggtgaccgag gcgatccagc gctggcgctg ttcgtcccag tgcagcccgc cgtctccacg    1260
gctgcggcgt ttggtcatgc ggcgactcct ttcttgcttt cctgttcgag cagggtgacg    1320
taggcggtga tggcgctggc cgggaccagc cgggtgcgac cctccttgac ggtgcgcaac    1380
cgccccgagc ggatcagttc atagatgacg gaacggctca agctcagcat ccgcatggct    1440
tccgggatgc ggtagagcgc cttcggggtg atgccgtcca acgggtgact cctccttttg    1500
cggcttcgat caggcggcgt tcaaggcgac aggccgggac gtgctcgctt cgtgcgcgag    1560
ttcctctcgg ccgatggctt gtcgctcgcg ggcctgagcc gcagcggtgt tggcgaggag    1620
tgcgtcgccg gtggtgtgcc agccgactcc ggcgaaggtc agggtgccga cgataagcgt    1680
ggtttcgtcg aggtggtcga cggtgtgcac ggtggcgttg tcggccggat cgggctcagc    1740
ccggcggaag tcgatgcgag tctcgcggag caggcggaag gtgaccgagt accggcgggc    1800
tttggtgagg aagtggccgc cgaagccgag catgtgcgcc cagcggcgga gccgggcgta    1860
tggggtgggc tggcggtcgt tgggccgttg ggtgtcaagg ctggcttgac gttcggcgac    1920
gcatacaggg caggtccggt agcgggtgcg ggtaccgcag tccggacagt ggcggggcgc    1980
tccaaagggc tgccggattt tggcaccggc ggtgccggtg tagacgggga gtcggatcgc    2040
cgttttgcca gctggggcgt cggggtcgtt gccgagatgc cagcaggcgt ggatgagccg    2100
ggcgatgtgg tctccggcgg gatcggcgtg ctgcgtgatg gtgtcgccgg tgatgcgcgt    2160
cgaattgtgg ccggtgatct cggtgctttt ggtggcgtac ttggcgaggt atccggcgac    2220
catgctgtcg gtgacttcgc cggtgccggt gaggctgatc gggcggatgt cgatctgttc    2280
gccccaggcc atcggccagc cgtccggccg gtcaggtggg tctggggtgg tgaagtcgat    2340
gtcgctggcg gcggtgagtg cgtcgaccag gtcgttgagg ccgatgccgg tggtggggc    2400 gacgacgcgg gtggggtcgg tggggtcgat gccgtcgagc cggatcaggg cgtggaagtg    2460
gaccgcgccg cggcgttgca tctcggcggc tttgccgtgg gcgaggcgga ccggtgggat    2520
ccggcgcagg ttttgccgt tgctgacctc gtggaacggg atgccgcggg ctttgcagag    2580
tttggcgagg cggcgttcgg cgtcctgttt ggtgcggtgc cagagttcgc cggagaacag    2640
gttccagacg acgtggtgct ggtggtcgta gcagtccagg cagaggggac ggccgagctg    2700
ggggtcgccg ggttcgtggc gtgcccagca gacggcgggt tggtagtgct ggcagaggcc    2760
ggggttgcgg cgggcgtggc agggttcggg gcggcagcta cagcgggcgc gattcgtgca    2820
ggtgtgtttg cggacgtggc gggtgtggac cgcgccgaag gagggggcgg tgagggtgac    2880
gaacacggcg gggtgccggg cgaccgtggt ggggacgcct ttgccgccga tgagcccggc    2940
gcgcaggatc tggaacgcgt cgcgctgcta ggtgcgggcg caggcgggc acacggtgga    3000 gcgccggtta ccgcaggcct tgtagatagc ggcatcggga agttggtcgg tgtgccggga    3060
gtcgagcagg cgcccgtgg tggcttcgat ggtgtcgagg gtgccggtga gccggaccgg    3120
gcgggtgcac ccgcggcgg cgcggacgtg gtcgagccag tcgaagtagc cgggttgggt    3180 ggcgcggtg agggcttggc cggctgcggt gtagtcggcg ggtggggtg tccaggcgtc    3240 ggcgttcgag cccgcacccc gggcagagtt ctccgggggt gcgaggtcca gcgtcgacgt    3300
gctcatgtca ggcagcgatc ctggtggtgg cgagctgcgg gccgtggtgg ccgacgaagg    3360
```

-continued

```
tgctggtgat gtgccgttcg atgacggtga tgcggcaggc cgggcattgc cgatggtggg    3420
gttcgtgacg gccgcagtcg ataacggcgg tcttgtcgcc gcagcggatg gagatggggt    3480
tgcggcaggg gccgccgtcg acggtggcga cgatggtgcg gcgggtgtcg aacgggtgca    3540
gctcagggtt ggctgggcag gtgtgggtga tgtggtggat gtcgacgtgg acgaaggtca    3600
tcgggcgccg ccggtcaggg tcgggatgtg cccgttgatg cgtgccgggt tggtgtcccg    3660
gatggtggtg atcagggttt cggcgacggc cggggtgatg ttgagtcgca gggcgaggtc    3720
gtcggcggtg atgggctggc cggtggtctg ctcgtgctgg acgaccgaga accgggcggc    3780
gggcagcagg tgagccggga cgaccggcgc ggtctgtggg gtggccggct gttcgaccgg    3840
agcggtcggg ccggtggtgg tgtgctccgg ttccggagtg gtcgccgtac cgcgggcttt    3900
gatcttgttg acgcggtca tgagttcggt ggcttgtttg tcgatggcgg tgaagtcggg    3960
gcggatgcgt ccggcgacga gttcgacgcc gatgaccacg acgacgacca gggcgaagac    4020
gatgcgcatg ccgaggtcgc cggggcggcg aagttgacgg tggccgagag cagggctgcg    4080
ccgatgaaga cggccatggc ccagcgtttg gcgtctttga cgatgccggg ggtgcggacg    4140
acgatcagca tcgagaccat ggcggtgtcg aagatcgccg ggggtaggta ggcgaagtag    4200
cccgcgccgg tgctggccag gtagtgggcc tggtggaggt agctggtgat cagtgcgccg    4260
atgagggtgc ctcggttgta gcgtttgacg ctgtcgatgg ccttgagcat gttcgggacg    4320
gcgctcttgg cgtactcgat ggcgaactgt tcggtgaggt tgacgctcgc gggggcggcc    4380
gggccggtgg tcggctgttg ggccgccttc ctgcggagag ggttcatcgg atgcctccgt    4440
cgttggtgac ggggatgacc gcgacgacgc ccatgcaggc ttcgcaccag acggcggaca    4500
ggccgtcgtc gaacagttcg ttgatgcggt cgtcgagggt ttcgtattcg gcggggaaca    4560
gcgacgtgct gccgcattcg tcgcaccact gctcggtcgg gcagaggcac aggaccgggc    4620
cgaggtccgg gtggataccg gcggggctca tgccgccgat gcaccacagg cagttgtcgg    4680
tggccaggtg cttgcccagg tcgatgaggc tcatcgtgag acctccggtg accggagcgc    4740
ctggtcggtc cagccgcaga cgtcacagtc gcggtagccg cagtactggc agcactgcga    4800
acgatcctgg tctttcggca tgacttctgc gcagtagtgg tcgccgcact ggcaccgtgt    4860
cgtagcgggg ctgttgtttt cagggtccgt ggtcatcggc tgcctcctac ttcgcagctc    4920
aggcagatac cggtgcggcg cgggatgtag tagtcacggg tgacgccgca ggagtcgcag    4980
gtgcggcggg cgagcagcat cttggcgacg accgcgagct gcgccgcggt gggaacacgt    5040
ttcggcttgc cgaggtcgcg ccggtagagg taggcgacgc ggcgttgtcc gcggtgcatc    5100
cacaggatct gggcgacggg gtcgtagccg ttggggcaga ggccgtcggc gcgcagctgg    5160
cgtcgggtgg ccaggtgctc gggcgcctgc cggtagggga aggtggggaa gccgtagcgg    5220
ctgccggtgg ggtcgtagaa ctcgacgcgg atgccggtgc gggcgccgag ggcttcgagg    5280
tagtcgttgg tcagggcgga ggtggtcatt tatcgcctcc ccagcgttgc tgggcggctt    5340
ggcgggagat gccgagccgg tcgccgattt cggcccagga atagccgtag gcgcgcaggc    5400
cgatgacggc ctcgctgatg gcgtcgtcga gctgggcgga gagtccgacc atgtcgcgca    5460
gggcttcgac gtcgccggtg gcgacgcgtt tggcgaaggc gcggatgatg cgccggacga    5520
aggcggcgta ttcgtcgttc tcgacgacgt cgcggcggcg cggcttcgaa ggccggctgt    5580
caccggccgg ggcggtaggt gtcaaggcag ggttgacgta cgacaggctc accgggcacc    5640
cccggtgtgg tgcagacgat cccagtcgtc agcggcgtcg gtgagggtct cgatgacctc    5700
```

-continued

```
gtcgcgggtg cggccctcgt agtcgttcca gtcgccgacg acgtcgatgg cgctggtctc    5760
gtagaagccg gtcggggtgt attccaggtc gagccaggcg gcgaagacgc gcagggcgcg    5820
gatggcggcg atggtgtcgg ggtcgccgtc gagggtgcac acgccggagg ccaggcagcg    5880
gccggtggcg gcggtcatga tcgcgccgga ggcgcaggcg ggcggaaact gcccgtcggt    5940
gatggcgacc aggtcgtaaa actggtgctg ggtccagccg tgctgctgga ggtagagggc    6000
ggcggcgcgc agcagcgcgg ccggggtcat cgtcgggtcg gtaacgggtg tgttggccgg    6060
ttgatgggta ggcttcatgg cagccacgtc ctttcgaggc tgttggtgga ggtcggcaga    6120
acccgcttgc ttgcaggctg tggggttct gtcgaccgct tccgttatgc ggttgtggtc     6180
cccggtgccg tccagcggcg aggatggtgc ttgcgcacat gggcggcggt gatcgccagg    6240
gcgaggacac cgaccggtgc ctggtgccgg gtgaggtggc cgacgagaag gccggcgagg    6300
taggcggtcg tggtggcggt ccagcgatt acgccggtga tggcctgagc gcgggtttcg      6360
gtcatgccgc catctcccat tgggtgcgcc cggtgtagga ggtcgtggtg gcgggattgg    6420
tagggcggcg tagccaggcg gcatagtcgg cgatggcgta gatgtcgtcg tcggacagcc    6480
aggccgcctt gatcgggtac gggagcttct tctcggcgcg cagcagggct tcgccggggt    6540
tgtcggggct gatggtggag gcgtcgaagc cgacctctgc gaggccggag ccgaggatga    6600
cgtcggagga gccgacggtg gtgcaccgga aggcgcagcg gtagccgaac aggtcccgca    6660
ggctggcggg gatgatgtcc caggagggc gctggtggc ccgacgacg gcatggcgc        6720
aggcgcggcc cagagcgacc aggccccgga gcagggtcga gaactcttcc tgttgggcct    6780
tggtgcctag cacggtcgag aacatcgcga tctcgtcgat gatggtgatg atcgtggaga    6840
ggttgtcctc ccgtgtgatt ttgcggcggc ggttggcgag cagccagcgg tagcggttgc    6900
gggcgacggt gagcaggcga cgcacggtct tgatggccag gtcgatgtcg tcgccgatga    6960
aggcgtccat gatcggttcc caggggccga gttcgaccca tttgccgtcc atgccgatca    7020
ggcgggtgtt gtcgctgagt gcggcggtcg ccgcgacgag gttgagcagg ccggacttgc    7080
cgccgccggg ctcaccagcg gtaagcaggt tgtggtagac gatgtcgagc gtgacgtgct    7140
cgccaaactc gtcgatgccg atgaacaggg gatcgaacat cgacatgcca ggcccgacag    7200
gcacccggtc ggtgccgagc ggatcgcagg cgatggtgct cacgagcttc gcctcccttc    7260
cggaggtgaa agggcaggac gctcgcggtg gagcgccctg cggtagggt cagatgggtt     7320
cggtggtgac gagcgggtcc cacccggatt cgcgtttcac ggccgacgcg cggcggcaga    7380
gttcggccac gagctggccg cagttgtgcg cgatggttcc caggcgggcg atcagctcgc    7440
cccgctgttg ttcggtgagc ccgtgatggc tcccgtcggt cacgtcccag ccgtcgtcga    7500
tgtagagctg ggcgagtccg ttgccgtcgc tgaacagccc ggcggtcatc caggccaggt    7560
cttccagggc ctgccgggag tcgatgtcgc tgacgatcag ttcgtcgttg acgaagtcgg    7620
tgacgccctg cggatcgagg cgttcgaggt gctgggtctg accgtagagg tcgaagatgc    7680
tcatacgggt gctcctcaga tccactggtt gatgtcgtcg ccgtcgtcgg cggcagtggc    7740
gggtttgcgg ccgttgctgc tggcagcggc ctgtttcggg atggccggct cggtggccgt    7800
cgggatgtcg tcgatgtcgg gcaggtcgag gccgtgaca gtggccgact ctttatcgtc      7860
gagcggcacg atcggatcga tctcgtcgat caggggggtg ctcaccttgg cggtgaggac    7920
ttcgcggcgc ttgatgtcga agcgcacgaa cgcagaattg gtgctaccgg ccaggtcgac    7980
cctgaccgtt ttggcatggc aggccacggc gatcttgccg acctgctgcg tgaggtaatc    8040
gaccgacagg ccggggccgca gtaggaccca gactcgttcc cccaccgggg tgggccaggc   8100
```

-continued

```
tccgaggatc agcgggaggc taccggagcg gttggtgatg atgaactgcg agaagcagac    8160
gcgcaggcga tgccgcacgg cgacacacca gaagatggcg acggtccagc ggcgcaggac    8220
cggaacgcag gccgggccgc cgaccaggac ggcaaggatg accgcggtca agatttgtga    8280
ggtactggcg gccagggcgg tccagcccca ggccagcagg acggtggctc cgatttcggg    8340
agtccaccac cagagcattc gcaggaccgg ccagctacgg accagtgccc agacgagggc    8400
gccgcagaca gcggcgatcg gagccgcgac gaacgcggcc agcagcgggt gcatgtggcc    8460
cttggccacg accagagcga ccaggccgct cacgatgacg gtgaagatga acgcgaaacg    8520
cgcgttctcg gcagccgagc gatgtacccg ctgctcgatg acggtgacag ttccggagcc    8580
tcgcccagaa cggccgggac gggtagattt ggacacgaca cgtcctccct tgcgggttgg    8640
atgggttcag gcgtggggcc ggatggtgtg cgaccgttac cggccccgcg ctttcttact    8700
ggtgatcagc gcccacgcgg gacgcgattg tcagcgctga gcgcgctggg gcttcggctg    8760
caccgagccg taccgggaga aggccataac cgtgaggcca ggaagaatgc ggccagcggc    8820
ctggttgatg aggtctttgg tctcgaggag atcaccctgt tcggtgatcg gattttttcga   8880 gtggatgtcg atggagccgt agcccccttg aacatgtag acacgtagt aacggaacat      8940 gatgggttcc tttcaaaaaa atgatgatgg ccgcatattg cggccggagg ccggaacgaa    9000
atcgctccgg ccatccgatg aatgagcagg gattacggca gcaaaaggcc gcctgggatc    9060
agatgccacg gacactgtgg cggcagtacg gatggggttg cgaagggcct acttcgccga    9120
ggcaccggag agcggcttca gcgacaccgc acggaacgcg acgccgttac gcccgttggt    9180
cgcccacgga atggcctcga gctgctcgat ggcgacgagc tgtcccaccg tcacgttcgg    9240
cttttcgcca gccgtcgtga tggcgatgac ctcgccgccg gtctcgtcga gcacgatgac    9300
ctgggtggac cacatgggcc ggccagtgtt cttctcggaa cgctggttgc cgttctggtc    9360
gttcttcggc tcggtcggct tcgacaccgt cacctgcttg ccggtcgtgt ccacgtacag    9420
cttcacgaag atctccttcg ttccagggat ccaactggaa tcccgaacct ttttgttgag    9480
ccgatcggct ccgccctcca tgaaacgcgg aaaattggcc ccgcagcagg tctccagatt    9540
tgatccgcgg agggcatcac tggctggcag tgactaggac tgactcgggc cttgcgaatg    9600
acacgtcgat agggcagtgt gaatgcggcg cattatcgac tctcacaggg cggaggctag    9660
agatgacgcc gctgcggctg gaaaggcaga agctcggctg gtcgagaacc cgccttgctc    9720
acgaactgga gcgacgggcg cagggaagat tcagcctggc caccagagcg agtcttctgc    9780
ggatgatctc agcgtgggaa agcggcgcgc gagacacctc ggacccgtat cgcactctgc    9840
tgtgcgaggc gtatggccgg accgctgacg agttgggcct gggtggtggc accgaccgag    9900
cagaatcgag cgtcggcctg tcctacgctt catcgcttga cgcggcagcc gcaatacttt    9960
ctgaccttgc ccggttcgat gacatgaagc accctgcggt gagccagggc cgctaccagc   10020
ccgatgcgtt gaacgcggta tgtctggact ggctgttcgg cacagcctcg aatgacatgc   10080
cagcaggcgc tggaaaacgc gtcaccatga aggacgtcga ggagatccgc gccaccacgt   10140
cgatgttcga cagcctggat cgccgattcg gaggggagaa cgcccgcagt atggccgtgc   10200
gttttctgcg cgaggcggtg ctgccagagat tcggcaaagac atccgaccag accgtaacta   10260
ctgagcttta cagagcagca gcgatcctct gcgagctgat cgggtggatg tcgttcgaca   10320
cctcacgcaa ctcgttggca cagcggtatt tcacccaagc gctgcgattg ccgaggcag    10380 ctggtgaccg cgcctatgcc tcgtacatct tggcgagcat ggcggaccaa gcgctcttcc   10440
```

```
tgaagaggcc tgaccaggcg ctacgacttg cacaggtcgc tcgcgatgcg ggggaaaagg    10500
ccggcgttgc ggtggccaca accgaggcga gcatgctgga ggctcgcgca ttcgcagccc    10560
agggtgacga gagcggctgc accagggcgt tgcttcgcgc ggaagccgcc ttcaacagca    10620
tcagcgcaga cgacaacccg agttgggcga accactgggg tgacatcttg tttgccagtc    10680
acgctggcac ctgttgggtc gatcttggtg cgccgaagga ggcagcgagc ttggttcgga    10740
cagtctggga cagcgcgaag gatcaggccc gtcgtcgggt ctacagcggc gttcagctcg    10800
ctcgcgtggc gctgcttacg aacgaggtgg aacaagcggt gtcgtatggg atcgccgccc    10860
ttgaggcgac gagcggcttg acttcgaatc gctcgttgca gcagcttcgc gacctgcgtg    10920
atcagcttgg aaaccatgcc aagcatcctg ctgttgtgga gttcgaggag cgcgctcgat    10980
tggtgctggc cgcttgagta ccgtaagcct cgtgacgttg gccgaggacc tggaccgcga    11040
aggtgaaccc gagcgggagt tcaacccccgg gatcgcgcag cgactaccta ggaagcgggt    11100
tgctggcgga gcgctgatcc gcgactcggc tgatcgaatc ctgttcgtcg tgccgaacta    11160
caagcccctg ctggacatcc ccggcggcat tgccgagggc aacgaatctc cgctcgcagc    11220
gtgccgacgt gagatcaagg aggagatcgg cctagacctg ccgatcggcc gacttctcgt    11280
ggtcgactgg atcccgcagc acggcgtgtg gccgacggc gtgatgttca tcttcgacgg    11340
cggccggcta accgacgacg agtcccgcga cctgaagcac accgatgatg agctggtagg    11400
actgaagttc cttgccctcg atgatgcacg ccatcagctt cggccctcaa tggttcgcag    11460
gctcgaagca gggatagagg ccttgtccga tggagagccg cggtatctgg agttcggtcg    11520
gactcagtaa agcggatggc cttaccgcg ttccatccgt tcggatgttc gggcgatggc    11580
tgcattgaga tcatcggcag cctcggtgat gaacgctgtc acgagatggc ccggcccgta    11640
acgttccttg atctcggcta cccgctcctc gaaggtcgtt cgttcccgt cgggtgtcgt    11700 ggtgagatcg cagaaccaga gggcgtcccg gaccggcgac gcctcgtcat ggaaagctgc    11760
aagttcctcc gcaaggcctc gcatcttggc ttcgcgtatc gcacacgaat ggtgcgctac    11820
aaggtgaaca agccgttccg gagcactgac ggaccgaagg aagtacgccc cgtctagcgg    11880
atggaaaccc gtctgcacga gatctggcgc atacccgatg tcgtggagta cagcagcagc    11940
ctcaagcaag cgggcatcgt cgccggcggc gttaccaaca gtacgagcct tcgccgcgac    12000
accttgaacg tgagaccagc gacgtggcag cacatccgcg aggacgcgtt cagacgtttg    12060
gtatgcccaa gcgaccatcg acatggaccc aacgatatcg gtgaactcgc agattcgtat    12120
gcgttgacgg agccggtcgg ctgccggatc ttgttcaaac tttctgtacg tcttcaaggc    12180
ggcccgaaac gggccgctca cgccgccgcc tgggcgcgtg ccggtcgctt agctggcgca    12240
cacgaccggc acgccggcag cccgtcggct ggcgtcagg agcggatcgg gccgcggcga    12300
cgacagtcca acaggcgggt tgaggctggg gagtttggcc gctgccgacc ggtgcggcca    12360
gggcgacgcg gccgagctgc cgccgcggcc gcagcgcga gtcacggccg tcggccgccg    12420
ggcgcggcgg cgcgcagtgt gtccgggccg ctcctccgag gtcaagggcg cttgcgtcg    12480 caagcgacgg ccgcaagcgg ccgccctgga cctcggagcc tctgcggccc tagcggccaa    12540
gtggtcaagc ggcaggccga tggcctgccc gcaggtggac gcgcgccacc gcacccggtc    12600 caccccgactc tgcaagaacc gttcgctact tcagcgtcaa tgaggaattg acaccttgga    12660 cgtcttttggc ggccaattcg caaaggcgct tgtgggcctc tccgaaagcg tcgattctgt    12720
attgtcgatc atcgcgcagc ttgatgaatt gttcctcgtg ctttggatta tctgccccca    12780
cttgcggtgc agcgcaaaag gtttgatatt ccttatgcgc tatggccgcc tgctcgaacg    12840
```

-continued

```
cccatcgcca ttcactcatg cacttcctaa attcggcagt gctgaatatc gaggcaagtg    12900
cgtccatgcg agcctgctcc ttggcgtcgc tcaaatcgtt tttgtactct tcatctgcaa    12960
taatgcatcg gcgtaattgg tcgcgagtaa gtgcaaacca cgttaccaac tccaagtaag    13020
ctgactttcg atcggcgtgc gcggcgatct ctctctggta aacccgttcg ctctgcttgc    13080
taaaattccc cagaaagaat tgaaacccgg ccccgctat cgcaaaaaat ccggttatca    13140
cagcgggcca gaagggtgtc atccgcattc ctcatctctg gatcaggctg acacgggctt    13200
ccatggtctc cgtgtgcgtc aagccctacg gtccagtagg actgcgaaca ggtgagttct    13260
cgccgcacgg ggacgcctcg ccgcctgcgc cttaagaccc tactgtggtg gacatgacgc    13320
gcaacatcga tgcagtgctt cgggtctcgc ctgcagacgg acgtggtat gtggacatcc     13380 ctgagttcaa cctgagagtg gatcttccgg cgtcaaggca agtagcgac ctgcgtaacc     13440 ggctaaacga cgccgtggca ccgcacgtgc ctgcggggac cgacttcgtg atcaagatgg    13500
cacctgagtg agtggcgcgc cttcctgagt gactaactgg gtgacaatcg ccaacgatca    13560
tggcggacaa gcgtggacgc tgatggacgt ggacccgcag gtgagcagtg tgttgaccaa    13620
gttcattcaa gatcatgagt tgc                                            13643
```

<210> SEQ ID NO 2
<211> LENGTH: 282
<212> TYPE: DNA
<213> ORGANISM: Actinoplanes sp. SE50/110

<400> SEQUENCE: 2

```
atggacgcac ttgcctcgat attcagcact gccgaattta ggaagtgcat gagtgaatgg     60
cgatgggcgt tcgagcaggc ggccatagcg cataaggaat atcaaaccctt ttgcgctgca   120 ccgcaagtgg ggccagataa tccaaagcac gaggaacaat tcatcaagct gcgcgatgat   180
cgacaataca gaatcgacgc tttcggagag gcccacaagc gcctttgcga attggccgcc   240
aaagacgtcc aaggtgtcaa ttcctcattg acgctgaagt ag                      282
```

<210> SEQ ID NO 3
<211> LENGTH: 771
<212> TYPE: DNA
<213> ORGANISM: Actinoplanes sp. SE50/110

<400> SEQUENCE: 3

```
atggaaaccc gtctgcacga gatctggcgc atacccgatg tcgtggagta cagcagcagc     60
ctcaagcaag cgggcatcgt cgccggcggc gttaccaaca gtacgagcct cgccgcgac    120 accttgaacg tgagaccagc gacgtggcag cacatccgcg aggacgcgtt cagacgtttg    180
gtatgcccaa gcgaccatcg acatggaccc aacgatatcg tgaactcgc agattcgtat    240 gcgttgacgg agccggtcgg ctgccggatc ttgttcaaac tttctgtacg tcttcaaggc    300
ggcccgaaac gggccgctca cgccgccgcc tgggcgcgtg ccggtcgctt agctggcgca    360
cacgaccggc acgccggcag cccgtcggct ggcgtgcagg agcggatcgg ccgcggcga     420 cgacagtcca acaggcgggt tgaggctggg gagtttggcc gctgccgacc ggtgcggcca    480
gggcgacgcg gccgagctgc cgcgcgcggc cgcagcgcga gtcacggccg tcggccgccg    540
ggcgcggcgg cgcgcagtgt gtccgggccg ctcctccgag gtcaagggcg cttcgcgtcg    600
caagcgacgg ccgcaagcgg ccgccctgga cctcggagcc tctgcggccc tagcggccaa    660
gtggtcaagc ggcaggccga tggcctgccc gcaggtggac gcgcgccacc gcacccggtc    720
```

```
cacccgactc tgcaagaacc gttcgctact tcagcgtcaa tgaggaattg a          771
```

<210> SEQ ID NO 4
<211> LENGTH: 243
<212> TYPE: DNA
<213> ORGANISM: Actinoplanes sp. SE50/110

<400> SEQUENCE: 4

```
atgcgaggcc ttgcggagga acttgcagct ttccatgacg aggcgtcgcc ggtccgggac   60
gccctctggt tctgcgatct caccacgaca cccgacgggg aacgaacgac cttcgaggag  120
cgggtagccg agatcaagga acgttacggg ccgggccatc tcgtgacagc gttcatcacc  180
gaggctgccg atgatctcaa tgcagccatc gcccgaacat ccgaacggat ggaacgccgg  240
taa                                                                243
```

<210> SEQ ID NO 5
<211> LENGTH: 519
<212> TYPE: DNA
<213> ORGANISM: Actinoplanes sp. SE50/110

<400> SEQUENCE: 5

```
gtgacgttgg ccgaggacct ggaccgcgaa ggtgaacccg agcgggagtt caaccccggg   60
atcgcgcagc gactacctag gaagcgggtt gctggcggag cgctgatccg cgactcggct  120
gatcgaatcc tgttcgtcgt gccgaactac aagcccctgc tggacatccc cggcggcatt  180
gccgagggca acgaatctcc gctcgcagcg tgccgacgtg agatcaagga ggagatcggc  240
ctagacctgc cgatcggccg acttctcgtg gtcgactgga tcccgcagca cggcgtgtgg  300
ccggacggcg tgatgttcat cttcgacggc ggccggctaa ccgacgacga gtcccgcgac  360
ctgaagcaca ccgatgatga ctggtagga ctgaagttcc ttgccctcga tgatgcacgc  420
catcagcttc ggccctcaat ggttcgcagg ctcgaagcag ggatagaggc cttgtccgat  480
ggagagccgc ggtatctgga gttcggtcgg actcagtaa                         519
```

<210> SEQ ID NO 6
<211> LENGTH: 1335
<212> TYPE: DNA
<213> ORGANISM: Actinoplanes sp. SE50/110

<400> SEQUENCE: 6

```
atgacgccgc tgcggctgga aaggcagaag ctcggctggt cgagaacccg ccttgctcac   60
gaactggagc gacgggcgca gggaagattc agcctggcca ccagacgag tcttctgcgg   120
atgatctcag cgtgggaaag cggcgcgcga cacacctcgg acccgtatcg cactctgctg  180
tgcgaggcgt atggccggac cgctgacgag ttgggcctgg gtggtggcac cgaccgagca  240
gaatcgagcg tcggcctgtc ctacgcttca tcgcttgacg cggcagccgc aatactttct  300
gaccttgccc ggttcgatga catgaagcac cctgcggtga ccagggccg ctaccagccc  360
gatgcgttga acgcggtatg tctggactgg ctgttcggca cagcctcgaa tgacatgcca  420
gcaggcgctg aaaacgcgt caccatgaag gacgtcgagg agatccgcgc caccacgtcg  480
atgttcgaca gcctggatcg ccgattcgga ggggagaacg cccgcagtat ggccgtgcgt  540
tttctgcgcg aggcggtgct gccgagattc ggcaagacat ccgaccagac cgtaactact  600
gagctttaca gagcagcagc gatcctctgc gagctgatcg ggtggatgtc gttcgacacc  660
tcacgcaact cgttgcaca gcggtatttc acccaagcgc tgcgattggc cgaggcagct  720
ggtgaccgcg cctatgcctc gtacatcttg gcgagcatgg cggaccaagc gctcttcctg  780
```

```
aagaggcctg accaggcgct acgacttgca caggtcgctc gcgatgcggg ggaaaaggcc    840
ggcgttgcgg tggccacaac cgaggcgagc atgctggagg ctcgcgcatt cgcagcccag    900
ggtgacgaga gcggctgcac cagggcgttg cttcgcgcgg aagccgcctt caacagcatc    960
agcgcagacg acaacccgag ttgggcgaac cactggggtg acatcttgtt tgccagtcac   1020
gctggcacct gttgggtcga tcttggtgcg ccgaaggagg cagcgagctt ggttcggaca   1080
gtctgggaca gcgcgaagga tcaggcccgt cgtcgggtct acagcggcgt tcagctcgct   1140
cgcgtggcgc tgcttacgaa cgaggtggaa caagcggtgt cgtatgggat cgccgccctt   1200
gaggcgacga gcggcttgac ttcgaatcgc tcgttcagc agcttcgcga cctgcgtgat   1260
cagcttggaa accatgccaa gcatcctgct gttgtggagt cgaggagcg cgctcgattg   1320 gtgctggccg cttga                                                    1335

<210> SEQ ID NO 7
<211> LENGTH: 318
<212> TYPE: DNA
<213> ORGANISM: Actinoplanes sp. SE50/110

<400> SEQUENCE: 7
gtgaagctgt acgtggacac gaccggcaag caggtgacgg tgtcgaagcc gaccgagccg     60
aagaacgacc agaacggcaa ccagcgttcc gagaagaaca ctggccggcc catgtggtcc    120
acccaggtca tcgtgctcga cgagaccggc ggcgaggtca tcgccatcac gacggctggc    180
gaaaagccga acgtgacggt gggacagctc gtcgccatcg agcagctcga ggccattccg    240
tgggcgacca acgggcgtaa cggcgtcgcg ttccgtgcgg tgtcgctgaa gccgctctcc    300
ggtgcctcgg cgaagtag                                                  318

<210> SEQ ID NO 8
<211> LENGTH: 210
<212> TYPE: DNA
<213> ORGANISM: Actinoplanes sp. SE50/110

<400> SEQUENCE: 8
atgttccgtt actacgtgtc ctacatgttc caagggggct acggctccat cgacatccac     60
tcgaaaaatc cgatcaccga acaggtgat ctcctcgaga ccaaagacct catcaaccag    120
gccgctggcc gcattcttcc tggcctcacg gttatggcct ctcccggta cggctcggtg    180 cagccgaagc cccagcgcgc tcagcgctga                                     210

<210> SEQ ID NO 9
<211> LENGTH: 921
<212> TYPE: DNA
<213> ORGANISM: Actinoplanes sp. SE50/110

<400> SEQUENCE: 9
gtgtccaaat ctacccgtcc cggccgttct gggcgaggct ccggaactgt caccgtcatc     60
gagcagcggg tacatcgctc ggctgccgag aacgcgcgtt tcgcgttcat cttcaccgtc    120
atcgtgagcg gcctggtcgc tctggtcgtg gccaagggcc acatgcaccc gctgctggcc    180
gcgttcgtcg cggctccgat cgccgctgtc tgcggcgccc tcgtctgggc actggtccgt    240
agctggccgg tcctgcgaat gctctggtgg tggactcccg aaatcggagc caccgtcctg    300
ctggcctggg gctggaccgc cctggccgcc agtacctcac aaatcttgac gcgcggtcatc    360 cttgccgtcc tggtcggcgg cccggcctgc gttccggtcc tgcgccgctg gaccgtcgcc    420
```

```
atcttctggt gtgtcgccgt gcggcatcgc ctgcgcgtct gcttctcgca gttcatcatc    480
accaaccgct ccgtagcct cccgctgatc ctcggagcct ggcccacccc ggtgggggaa     540
cgagtctggg tcctactgcg gcccggcctg tcggtcgatt acctcacgca gcaggtcggc    600
aagatcgccg tggcctgcca tgccaaaacg gtcagggtcg acctggccgg tagcaccaat    660
tctgcgttcg tgcgcttcga catcaagcgc cgcgaagtcc tcaccgccaa ggtgagcacc    720
cccctgatcg acgagatcga tccgatcgtg ccgctcgacg ataaagagtc ggccactgtc    780
acgggcctcg acctgcccga catcgacgac atcccgacgg ccaccgagcc ggccatcccg    840
aaacaggccg ctgccagcag caacggccgc aaacccgcca ctgccgccga cgacggcgac    900
gacatcaacc agtggatctg a                                               921

<210> SEQ ID NO 10
<211> LENGTH: 375
<212> TYPE: DNA
<213> ORGANISM: Actinoplanes sp. SE50/110

<400> SEQUENCE: 10
atgagcatct tcgacctcta cggtcagacc cagcacctcg aacgcctcga tccgcagggc     60
gtcaccgact tcgtcaacga cgaactgatc gtcagcgaca tcgactcccg gcaggccctg    120
gaagacctgg cctggatgac cgccgggctg ttcagcgacg gcaacggact cgcccagctc    180
tacatcgaca cggctgggga cgtgaccgac gggagccatc acgggctcac cgaacaacag    240
cggggcgagc tgatcgcccg cctgggaacc atcgcgcaca actgcggcca gctcgtggcc    300
gaactctgcc gccgcgcgtc ggccgtgaaa cgcgaatccg ggtgggaccc gctcgtcacc    360 accgaacccca tctga                                                    375

<210> SEQ ID NO 11
<211> LENGTH: 882
<212> TYPE: DNA
<213> ORGANISM: Actinoplanes sp. SE50/110

<400> SEQUENCE: 11
gtgagcacca tcgcctgcga tccgctcggc accgaccggg tgcctgtcgg gcctggcatg     60
tcgatgttcg atccctgtt catcggcatc gacgagtttg gcgagcacgt cacgctcgac    120
atcgtctacc acaacctgct taccgctggt gagcccggcg gcggcaagtc cggcctgctc    180
aacctcgtcg cggcgaccgc cgcactcagc gacaacaccc gcctgatcgg catggacggc    240
aaatgggtcg aactcggccc ctgggaaccg atcatggacg ccttcatcgg cgacgacatc    300
gacctggcca tcaagaccgt gcgtcgcctg ctcaccgtcg cccgcaaccg ctaccgctgg    360
ctgctcgcca accgccgccg caaaatcaca cgggaggaca acctctccac gatcatcacc    420
atcatcgacg agatcgcgat gttctcgacc gtgctaggca ccaaggccca acaggaagag    480
ttctcgaccc tgctccgggg cctggtcgct ctgggccgcg cctgcgccat gcccgtcgtc    540
ggcgccaccc agcgcccctc ctgggacatc atccccgcca gcctgcggga cctgttcggc    600
taccgctgcg ccttccggtg caccaccgtc ggctcctccg acgtcatcct cggctccggc    660
ctcgcagagg tcggcttcga cgcctccacc atcagcccg acaacccgg cgaagccctg    720 ctgcgcgccg agaagaagct cccgtacccg atcaaggcgg cctggctgtc cgacgacgac    780
atctacgcca tcgccgacta tgccgcctgg ctacgccgcc ctaccaatcc cgccaccacg    840
acctcctaca ccgggcgcac ccaatgggag atggcggcat ga                       882
```

<210> SEQ ID NO 12
<211> LENGTH: 201
<212> TYPE: DNA
<213> ORGANISM: Actinoplanes sp. SE50/110

<400> SEQUENCE: 12

```
atgaccgaaa cccgcgctca ggccatcacc ggcgtaatcg ctggaaccgc caccacgacc      60
gcctacctcg ccggccttct cgtcggccac ctcacccggc accaggcacc ggtcggtgtc     120
ctcgccctgg cgatcaccgc cgcccatgtg cgcaagcacc atcctcgccg ctggacggca     180
ccggggacca caaccgcata a                                               201
```

<210> SEQ ID NO 13
<211> LENGTH: 450
<212> TYPE: DNA
<213> ORGANISM: Actinoplanes sp. SE50/110

<400> SEQUENCE: 13

```
atgaagccta cccatcaacc ggccaacaca cccgttaccg acccgacgat gaccccggcc      60
gcgctgctgc gcgccgccgc cctctacctc cagcagcacg gctggaccca gcaccagttt     120
tacgacctgg tcgccatcac cgacgggcag tttccgcccg cctgcgcctc cggcgcgatc     180
atgaccgccg ccaccggccg ctgcctggcc tccggcgtgt gcaccctcga cggcgacccc     240
gacaccatcg ccgccatccg cgccctgcgc gtcttcgccg cctggctcga cctggaatac     300
accccgaccg gcttctacga ccagcgcc atcgacgtcg tcggcgactg gaacgactac     360
gagggccgca cccgcgacga ggtcatcgag accctcaccg acgccgctga cgactgggat     420
cgtctgcacc acaccggggg tgcccggtga                                      450
```

<210> SEQ ID NO 14
<211> LENGTH: 327
<212> TYPE: DNA
<213> ORGANISM: Actinoplanes sp. SE50/110

<400> SEQUENCE: 14

```
gtgagcctgt cgtacgtcaa ccctgccttg acacctaccg ccccggccgg tgacagccgg      60
ccttcgaagc cgcgccgccg cgacgtcgtc gagaacgacg aatacgccgc cttcgtccgg     120
cgcatcatcc gcgccttcgc caaacgcgtc gccaccggcg acgtcgaagc cctgcgcgac     180
atggtcggac tctccgccca gctcgacgac gccatcagca aggccgtcat cggcctgcgc     240
gcctacggct attcctgggc cgaaatcggc gaccggctcg gcatctcccg ccaagccgcc     300
cagcaacgct ggggaggcga taaatga                                         327
```

<210> SEQ ID NO 15
<211> LENGTH: 417
<212> TYPE: DNA
<213> ORGANISM: Actinoplanes sp. SE50/110

<400> SEQUENCE: 15

```
atgaccacct ccgccctgac caacgactac ctcgaagccc tcggcgcccg caccggcatc      60
cgcgtcgagt tctacgaccc caccggcagc cgctacggct cccccacctt ccccctaccgg     120
caggcgccca gcacctggc cacccgacgc cagctgcgcg ccgacggcct ctgccccaac     180
ggctacgacc ccgtcgccca gatcctgtgg atgaccgcg acaacgccg gtcgcctac     240
ctctaccggc gcgacctcgc caagccgaaa cgtgttccca ccgcggcgca gctcgcggtc     300
gtcgccaaga tgctgctcgc ccgccgcacc tgcgactcct gcggcgtcac ccgtgactac     360
```

```
tacatcccgc gccgcaccgg tatctgcctg agctgcgaag taggaggcag ccgatga      417

<210> SEQ ID NO 16
<211> LENGTH: 186
<212> TYPE: DNA
<213> ORGANISM: Actinoplanes sp. SE50/110

<400> SEQUENCE: 16
atgaccacgg accctgaaaa caacagcccc gctacgacac ggtgccagtg cggcgaccac      60
tactgcgcag aagtcatgcc gaaagaccag gatcgttcgc agtgctgcca gtactgcggc      120
taccgcgact gtgacgtctg cggctggacc gaccaggcgc tccggtcacc ggaggtctca      180
cgatga                                                                186

<210> SEQ ID NO 17
<211> LENGTH: 291
<212> TYPE: DNA
<213> ORGANISM: Actinoplanes sp. SE50/110

<400> SEQUENCE: 17
atgagcctca tcgacctggg caagcacctg gccaccgaca actgcctgtg gtgcatcggc      60
ggcatgagcc ccgccggtat ccacccggac ctcggcccgg tcctgtgcct ctgcccgacc     120
gagcagtggt gcgacgaatg cggcagcacg tcgctgttcc ccgccgaata cgaaaccctc     180
gacgaccgca tcaacgaact gttcgacgac ggcctgtccg ccgtctggtg cgaagcctgc     240
atgggcgtcg tcgcggtcat ccccgtcacc aacgacggag gcatccgatg a              291

<210> SEQ ID NO 18
<211> LENGTH: 510
<212> TYPE: DNA
<213> ORGANISM: Actinoplanes sp. SE50/110

<400> SEQUENCE: 18
atgaaccctc tccgcaggaa ggcggcccaa cagccgacca ccggcccggc cgccccgcg       60 agcgtcaacc tcaccgaaca gttcgccatc gagtacgcca agagcgccgt cccgaacatg     120
ctcaaggcca tcgacagcgt caaacgctac aaccgagcca ccctcatcgg cgcactgatc     180
accagctacc tccaccaggc ccactacctg gccagcaccg gcgcgggcta cttcgcctac     240 ctaccccgg cgatcttcga caccgccatg gtctcgatgc tgatcgtcgt ccgcaccccc      300
ggcatcgtca agacgccaa acgctgggcc atggccgtct tcatcggcgc agccctgctc      360
tcggccaccg tcaacttcgc cgccccggcg acctcggcat cgcatcgtc ttcgccctgg     420 tcgtcgtcgt ggtcatcggc gtcgaactcg tcgccggacg catccgcccc gacttcaccg     480
ccatcgacaa caagccacc gaactcatga                                       510

<210> SEQ ID NO 19
<211> LENGTH: 324
<212> TYPE: DNA
<213> ORGANISM: Actinoplanes sp. SE50/110

<400> SEQUENCE: 19
atgaccgccg tcaacaagat caaagcccgc ggtacggcga ccactccgga accggagcac      60
accaccaccg gcccgaccgc tccggtcgaa cagccggcca cccacagac cgcgccggtc      120 gtcccggctc acctgctgcc cgccgccgg ttctcggtcg tccagcacga gcagaccacc      180
ggccagccca tcaccgccga cgacctcgcc ctgcgactca acatcacccc ggccgtcgcc      240 gaaacccctga tcaccaccat ccgggacacc aacccggcac gcatcaacgg gcacatcccg     300
```

| | |
|---|---|
| accctgaccg gcggcgcccg atga | 324 |

<210> SEQ ID NO 20
<211> LENGTH: 294
<212> TYPE: DNA
<213> ORGANISM: Actinoplanes sp. SE50/110

<400> SEQUENCE: 20

| | |
|---|---|
| atgaccttcg tccacgtcga catccaccac atcacccaca cctgcccagc caaccctgag | 60 |
| ctgcacccgt tcgacacccg ccgcaccatc gtcgccaccg tcgacggcgg ccccctgccgc | 120 |
| aaccccatct ccatccgctg cggcgacaag accgccgtta tcgactgcgg ccgtcacgaa | 180 |
| ccccaccatc ggcaatgccc ggcctgccgc atcaccgtca tcgaacggca catcaccagc | 240 |
| accttcgtcg ccaccacgg cccgcagctc gccaccacca ggatcgctgc ctga | 294 |

<210> SEQ ID NO 21
<211> LENGTH: 1797
<212> TYPE: DNA
<213> ORGANISM: Actinoplanes sp. SE50/110

<400> SEQUENCE: 21

| | |
|---|---|
| atgagcacgt cgacgctgga cctcgcaccc cgggagaact ctgcccgggg tgcgggctcg | 60 |
| aacgccgacg cctggacacc cccacccgcc gactacaccg cagccggcca agccctcacc | 120 |
| cgcgccaccc aacccggcta cttcgactgg ctcgaccacg tccgcgccgc cgccgggtgc | 180 |
| acccgcccgg tccggctcac cggcaccctc gacaccatcg aagccaccac cgggcgcctg | 240 |
| ctcgactccc ggcacaccga ccaacttccc gatgccgcta tctacaaggc ctgcggtaac | 300 |
| cggcgctcca ccgtgtgccc cgcctgcgcc cgcacctacc agcgcgacgc gttccagatc | 360 |
| ctgcgcgccg ggctcatcgg cggcaaaggc gtccccacca cggtcgcccg gcaccccgcc | 420 |
| gtgttcgtca ccctcaccgc cccctccttc ggcgcggtcc acacccgcca cgtccgcaaa | 480 |
| cacacctgca cgaatcgcgc ccgctgtagc tgccgccccg aaccctgcca cgcccgccgc | 540 |
| aaccccggcc tctgccagca ctaccaaccc gccgtctgct gggcacgcca cgaacccggc | 600 |
| gacccccagc tcggccgtcc cctctgcctg gactgctacg accaccagca ccacgtcgtc | 660 |
| tggaacctgt tctccggcga actctggcac cgcaccaaac aggacgccga acgccgcctc | 720 |
| gccaaactct gcaaagcccg cggcatcccg ttccacgagg tcagcaacgg caaaaacctg | 780 |
| cgccggatcc caccggtccg cctcgcccac ggcaaagccg ccgagatgca acgccgcggc | 840 |
| gcggtccact ccacgccct gatccggctc gacggcatcg accccaccga ccccacccgc | 900 |
| gtcgtcgccc caccacccgg catcggcctc aacgacctgg tcgacgcact caccgccgcc | 960 |
| agcgacatcg acttcaccac cccagaccac cctgaccggc cggacggctg gccgatggcc | 1020 |
| tggggcgaac agatcgacat ccgcccgatc agcctcaccg gcaccggcga agtcaccgac | 1080 |
| agcatggtcg ccggatacct cgccaagtac gccaccaaaa gcaccgagat caccggccac | 1140 |
| aattcgacgc gcatcaccgg cgacaccatc acgcagcacg ccgatcccgc cggagaccac | 1200 |
| atcgcccggc tcatccacgc ctgctggcat ctcggcaacg accccgacgc ccagctggc | 1260 |
| aaaacggcga tccgactccc cgtctacacc ggcaccgccg gtgccaaaat ccggcagccc | 1320 |
| tttggagcgc cccgccactg tccggactgc ggtacccgca cccgctaccg gacctgccct | 1380 |
| gtatgcgtcg ccgaacgtca agccagcctt gacacccaac ggcccaacga ccgccagccc | 1440 |
| accccatacg cccggctccg ccgctgggcg cacatgctcg gcttcggcgg ccacttcctc | 1500 |

```
accaaagccc gccggtactc ggtcaccttc cgcctgctcc gcgagactcg catcgacttc    1560
cgccgggctg agcccgatcc ggccgacaac gccaccgtgc acaccgtcga ccacctcgac    1620
gaaaccacgc ttatcgtcgg caccctgacc ttcgccggag tcggctggca caccaccggc    1680
gacgcactcc tcgccaacac cgctgcggct caggcccgcg agcgacaagc catcggccga    1740
gaggaactcg cgcacgaagc gagcacgtcc cggcctgtcg ccttgaacgc cgcctga      1797
```

<210> SEQ ID NO 22
<211> LENGTH: 207
<212> TYPE: DNA
<213> ORGANISM: Actinoplanes sp. SE50/110

<400> SEQUENCE: 22

```
ttggacggca tcaccccgaa ggcgctctac cgcatcccgg aagccatgcg gatgctgagc      60
ttgagccgtt ccgtcatcta tgaactgatc cgctcggggc ggttgcgcac cgtcaaggag    120
ggtcgcaccc ggctggtccc ggccagcgcc atcaccgcct acgtcaccct gctcgaacag    180
gaaagcaaga aggagtcgc cgcatga                                          207
```

<210> SEQ ID NO 23
<211> LENGTH: 1167
<212> TYPE: DNA
<213> ORGANISM: Actinoplanes sp. SE50/110

<400> SEQUENCE: 23

```
atgaccaaac gccgcagccg tggagacggc gggctgcact gggacgaaca gcgccagcgc      60
tggatcgcct cggtcaccgt cggatacacc ccggccggta aacgcatcgt ccgtaaggca    120
agcggcaaga ccaagaccga ggccaacaat gcactccgtc agaagatccg tgagtaccag    180
gacgggctgt cgatccccac gaccggctac acggtcgccg acgccgtcac ggactggctc    240
acctacggac ttcccgacgt cgacgaggaa acggtcaaca actacacgct gctggccaac    300
ggtcacatca tcccggcgat cggtgcacgc aagctccgtg accccagcaa acagaaggaa    360
ctcagcgcca ccgacattga caggtggctg gccgacaaag ccaagattct cagcacccgc    420
acgctgcgac tgctgcactc gatcgcgaat cgcgccatca accgagcgat ggcccgcgac    480
aaggtcatgc gcaacgtcgt cgcactctgc aaggtaccga ccggcaccgc cggacgaccc    540
tccaagtcac tcacctacga gcaggccaaa gcgctcctcg tcgctgccga gtcgagcagc    600
ctgcacgcgt atgtagtttt gtcgctgctg accggtgctc gtaccgagga actgcgagaa    660
ctcacctggc agcacgtcga cctggtcgga cgtccggacg ccgagccacc gattccgccg    720
gccatccacg tatggcattc ggtgcgcgcc cacggtgaca ccaagaccaa gaagtcacgg    780
cgttcactcg ccctgccggt tcgctgtgtc cgggtcctca ccgcgcaacg cgcggcgcac    840
ggagatccac gaccggatga ctacgtctgc gccagcaagg tcggcaccca gctcgaccgg    900
cacaacgtgc tgcgagcctt ccgcgcgatc gtcgcggctg tccccggaat gaatccggct    960
gaatggacgc cccgcgaatt acggcacagt ttcgtttcgc tgctgtccga caatgggatg   1020
agcatcgagg aaatcgccga cctgtgtggt cattccggca cctcgatcac cgagaccgtt   1080
taccgccacc aactgcgccc ggttctgctg aacggcgcgg tggccatgga ccggatcttc   1140
ggtccggatg acactcctgg ggcttag                                         1167
```

<210> SEQ ID NO 24
<211> LENGTH: 93
<212> TYPE: PRT
<213> ORGANISM: Actinoplanes sp. SE50/110

<400> SEQUENCE: 24

Met Asp Ala Leu Ala Ser Ile Phe Ser Thr Ala Glu Phe Arg Lys Cys
1               5                   10                  15

Met Ser Glu Trp Arg Trp Ala Phe Glu Gln Ala Ala Ile Ala His Lys
                20                  25                  30

Glu Tyr Gln Thr Phe Cys Ala Ala Pro Gln Val Gly Pro Asp Asn Pro
            35                  40                  45

Lys His Glu Glu Gln Phe Ile Lys Leu Arg Asp Asp Arg Gln Tyr Arg
    50                  55                  60

Ile Asp Ala Phe Gly Glu Ala His Lys Arg Leu Cys Glu Leu Ala Ala
65                  70                  75                  80

Lys Asp Val Gln Gly Val Asn Ser Ser Leu Thr Leu Lys
                85                  90

<210> SEQ ID NO 25
<211> LENGTH: 256
<212> TYPE: PRT
<213> ORGANISM: Actinoplanes sp. SE50/110

<400> SEQUENCE: 25

Met Glu Thr Arg Leu His Glu Ile Trp Arg Ile Pro Asp Val Val Glu
1               5                   10                  15

Tyr Ser Ser Ser Leu Lys Gln Ala Gly Ile Val Ala Gly Gly Val Thr
                20                  25                  30

Asn Ser Thr Ser Leu Arg Arg Asp Thr Leu Asn Val Arg Pro Ala Thr
            35                  40                  45

Trp Gln His Ile Arg Glu Asp Ala Phe Arg Arg Leu Val Cys Pro Ser
    50                  55                  60

Asp His Arg His Gly Pro Asn Asp Ile Gly Leu Ala Asp Ser Tyr
65                  70                  75                  80

Ala Leu Thr Glu Pro Val Gly Cys Arg Ile Leu Phe Lys Leu Ser Val
                85                  90                  95

Arg Leu Gln Gly Gly Pro Lys Arg Ala Ala His Ala Ala Ala Trp Ala
            100                 105                 110

Arg Ala Gly Arg Leu Ala Gly Ala His Asp Arg His Ala Gly Ser Pro
    115                 120                 125

Ser Ala Gly Val Gln Glu Arg Ile Gly Pro Arg Arg Gln Ser Asn
    130                 135                 140

Arg Arg Val Glu Ala Gly Glu Phe Gly Arg Cys Arg Pro Val Arg Pro
145                 150                 155                 160

Gly Arg Arg Gly Arg Ala Ala Ala Arg Gly Arg Ser Ala Ser His Gly
                165                 170                 175

Arg Arg Pro Pro Gly Ala Ala Ala Arg Ser Val Ser Gly Pro Leu Leu
            180                 185                 190

Arg Gly Gln Gly Arg Phe Ala Ser Gln Ala Thr Ala Ala Ser Gly Arg
    195                 200                 205

Pro Gly Pro Arg Ser Leu Cys Gly Pro Ser Gly Gln Val Val Lys Arg
    210                 215                 220

Gln Ala Asp Gly Leu Pro Ala Gly Gly Arg Ala Pro His Pro Val
225                 230                 235                 240

His Pro Thr Leu Gln Glu Pro Phe Ala Thr Ser Ala Ser Met Arg Asn
                245                 250                 255

<210> SEQ ID NO 26

```
<211> LENGTH: 80
<212> TYPE: PRT
<213> ORGANISM: Actinoplanes sp. SE50/110

<400> SEQUENCE: 26

Met Arg Gly Leu Ala Glu Glu Leu Ala Ala Phe His Asp Glu Ala Ser
1               5                   10                  15

Pro Val Arg Asp Ala Leu Trp Phe Cys Asp Leu Thr Thr Thr Pro Asp
            20                  25                  30

Gly Glu Arg Thr Thr Phe Glu Arg Val Ala Glu Ile Lys Glu Arg
            35                  40                  45

Tyr Gly Pro Gly His Leu Val Thr Ala Phe Ile Thr Glu Ala Ala Asp
50                  55                  60

Asp Leu Asn Ala Ala Ile Ala Arg Thr Ser Glu Arg Met Glu Arg Arg
65                  70                  75                  80

<210> SEQ ID NO 27
<211> LENGTH: 172
<212> TYPE: PRT
<213> ORGANISM: Actinoplanes sp. SE50/110

<400> SEQUENCE: 27

Met Thr Leu Ala Glu Asp Leu Asp Arg Glu Gly Glu Pro Glu Arg Glu
1               5                   10                  15

Phe Asn Pro Gly Ile Ala Gln Arg Leu Pro Arg Lys Arg Val Ala Gly
            20                  25                  30

Gly Ala Leu Ile Arg Asp Ser Ala Asp Arg Ile Leu Phe Val Val Pro
            35                  40                  45

Asn Tyr Lys Pro Leu Leu Asp Ile Pro Gly Gly Ile Ala Glu Gly Asn
50                  55                  60

Glu Ser Pro Leu Ala Ala Cys Arg Arg Glu Ile Lys Glu Glu Ile Gly
65                  70                  75                  80

Leu Asp Leu Pro Ile Gly Arg Leu Leu Val Val Asp Trp Ile Pro Gln
                85                  90                  95

His Gly Val Trp Pro Asp Gly Val Met Phe Ile Phe Asp Gly Gly Arg
            100                 105                 110

Leu Thr Asp Asp Glu Ser Arg Asp Leu Lys His Thr Asp Asp Glu Leu
            115                 120                 125

Val Gly Leu Lys Phe Leu Ala Leu Asp Asp Ala Arg His Gln Leu Arg
            130                 135                 140

Pro Ser Met Val Arg Arg Leu Glu Ala Gly Ile Glu Ala Leu Ser Asp
145                 150                 155                 160

Gly Glu Pro Arg Tyr Leu Glu Phe Gly Arg Thr Gln
                165                 170

<210> SEQ ID NO 28
<211> LENGTH: 444
<212> TYPE: PRT
<213> ORGANISM: Actinoplanes sp. SE50/110

<400> SEQUENCE: 28

Met Thr Pro Leu Arg Leu Glu Arg Gln Lys Leu Gly Trp Ser Arg Thr
1               5                   10                  15

Arg Leu Ala His Glu Leu Glu Arg Arg Ala Gln Gly Arg Phe Ser Leu
            20                  25                  30

Ala Thr Arg Ala Ser Leu Leu Arg Met Ile Ser Ala Trp Glu Ser Gly
            35                  40                  45
```

```
Ala Arg Asp Thr Ser Asp Pro Tyr Arg Thr Leu Leu Cys Glu Ala Tyr
 50                  55                  60
Gly Arg Thr Ala Asp Glu Leu Gly Leu Gly Gly Thr Asp Arg Ala
 65                  70                  75                  80
Glu Ser Ser Val Gly Leu Ser Tyr Ala Ser Ser Leu Asp Ala Ala Ala
                 85                  90                  95
Ala Ile Leu Ser Asp Leu Ala Arg Phe Asp Met Lys His Pro Ala
                100                 105                 110
Val Ser Gln Gly Arg Tyr Gln Pro Asp Ala Leu Asn Ala Val Cys Leu
                115                 120                 125
Asp Trp Leu Phe Gly Thr Ala Ser Asn Asp Met Pro Ala Gly Ala Gly
130                 135                 140
Lys Arg Val Thr Met Lys Asp Val Glu Glu Ile Arg Ala Thr Thr Ser
145                 150                 155                 160
Met Phe Asp Ser Leu Asp Arg Arg Phe Gly Glu Asn Ala Arg Ser
                165                 170                 175
Met Ala Val Arg Phe Leu Arg Glu Ala Val Leu Pro Arg Phe Gly Lys
                180                 185                 190
Thr Ser Asp Gln Thr Val Thr Thr Glu Leu Tyr Arg Ala Ala Ile
                195                 200                 205
Leu Cys Glu Leu Ile Gly Trp Met Ser Phe Asp Thr Ser Arg Asn Ser
210                 215                 220
Leu Ala Gln Arg Tyr Phe Thr Gln Ala Leu Arg Leu Ala Glu Ala Ala
225                 230                 235                 240
Gly Asp Arg Ala Tyr Ala Ser Tyr Ile Leu Ala Ser Met Ala Asp Gln
                245                 250                 255
Ala Leu Phe Leu Lys Arg Pro Asp Gln Ala Leu Arg Leu Ala Gln Val
                260                 265                 270
Ala Arg Asp Ala Gly Glu Lys Ala Gly Val Ala Val Ala Thr Thr Glu
                275                 280                 285
Ala Ser Met Leu Glu Ala Arg Ala Phe Ala Ala Gln Gly Asp Glu Ser
                290                 295                 300
Gly Cys Thr Arg Ala Leu Leu Arg Ala Glu Ala Ala Phe Asn Ser Ile
305                 310                 315                 320
Ser Ala Asp Asp Asn Pro Ser Trp Ala Asn His Trp Gly Asp Ile Leu
                325                 330                 335
Phe Ala Ser His Ala Gly Thr Cys Trp Val Asp Leu Gly Ala Pro Lys
                340                 345                 350
Glu Ala Ala Ser Leu Val Arg Thr Val Trp Asp Ser Ala Lys Asp Gln
                355                 360                 365
Ala Arg Arg Arg Val Tyr Ser Gly Val Gln Leu Ala Arg Val Ala Leu
                370                 375                 380
Leu Thr Asn Glu Val Glu Gln Ala Val Ser Tyr Gly Ile Ala Ala Leu
385                 390                 395                 400
Glu Ala Thr Ser Gly Leu Thr Ser Asn Arg Ser Leu Gln Gln Leu Arg
                405                 410                 415
Asp Leu Arg Asp Gln Leu Gly Asn His Ala Lys His Pro Ala Val Val
                420                 425                 430
Glu Phe Glu Glu Arg Ala Arg Leu Val Leu Ala Ala
                435                 440

<210> SEQ ID NO 29
<211> LENGTH: 105
<212> TYPE: PRT
```

<213> ORGANISM: Actinoplanes sp. SE50/110

<400> SEQUENCE: 29

Met Lys Leu Tyr Val Asp Thr Thr Gly Lys Gln Val Thr Ser Lys
1               5                   10                  15

Pro Thr Glu Pro Lys Asn Asp Gln Asn Gly Asn Gln Arg Ser Glu Lys
            20                  25                  30

Asn Thr Gly Arg Pro Met Trp Ser Thr Gln Val Ile Val Leu Asp Glu
        35                  40                  45

Thr Gly Gly Glu Val Ile Ala Ile Thr Thr Ala Gly Glu Lys Pro Asn
    50                  55                  60

Val Thr Val Gly Gln Leu Val Ala Ile Glu Gln Leu Glu Ala Ile Pro
65                  70                  75                  80

Trp Ala Thr Asn Gly Arg Asn Gly Val Ala Phe Arg Ala Val Ser Leu
                85                  90                  95

Lys Pro Leu Ser Gly Ala Ser Ala Lys
            100                 105

<210> SEQ ID NO 30
<211> LENGTH: 69
<212> TYPE: PRT
<213> ORGANISM: Actinoplanes sp. SE50/110

<400> SEQUENCE: 30

Met Phe Arg Tyr Tyr Val Ser Tyr Met Phe Gln Gly Gly Tyr Gly Ser
1               5                   10                  15

Ile Asp Ile His Ser Lys Asn Pro Ile Thr Glu Gln Gly Asp Leu Leu
            20                  25                  30

Glu Thr Lys Asp Leu Ile Asn Gln Ala Ala Gly Arg Ile Leu Pro Gly
        35                  40                  45

Leu Thr Val Met Ala Phe Ser Arg Tyr Gly Ser Val Gln Pro Lys Pro
    50                  55                  60

Gln Arg Ala Gln Arg
65

<210> SEQ ID NO 31
<211> LENGTH: 306
<212> TYPE: PRT
<213> ORGANISM: Actinoplanes sp. SE50/110

<400> SEQUENCE: 31

Met Ser Lys Ser Thr Arg Pro Gly Arg Ser Gly Arg Gly Ser Gly Thr
1               5                   10                  15

Val Thr Val Ile Glu Gln Arg Val His Arg Ser Ala Ala Glu Asn Ala
            20                  25                  30

Arg Phe Ala Phe Ile Phe Thr Val Ile Val Ser Gly Leu Val Ala Leu
        35                  40                  45

Val Val Ala Lys Gly His Met His Pro Leu Leu Ala Ala Phe Val Ala
    50                  55                  60

Ala Pro Ile Ala Ala Val Cys Gly Ala Leu Val Trp Ala Leu Val Arg
65                  70                  75                  80

Ser Trp Pro Val Leu Arg Met Leu Trp Trp Thr Pro Glu Ile Gly
                85                  90                  95

Ala Thr Val Leu Leu Ala Trp Gly Trp Thr Ala Leu Ala Ala Ser Thr
            100                 105                 110

Ser Gln Ile Leu Thr Ala Val Ile Leu Ala Val Leu Val Gly Gly Pro
        115                 120                 125

```
Ala Cys Val Pro Val Leu Arg Arg Trp Thr Val Ala Ile Phe Trp Cys
    130                 135                 140

Val Ala Val Arg His Arg Leu Arg Val Cys Phe Ser Gln Phe Ile Ile
145                 150                 155                 160

Thr Asn Arg Ser Gly Ser Leu Pro Leu Ile Leu Gly Ala Trp Pro Thr
                165                 170                 175

Pro Val Gly Glu Arg Val Trp Val Leu Leu Arg Pro Gly Leu Ser Val
            180                 185                 190

Asp Tyr Leu Thr Gln Gln Val Gly Lys Ile Ala Val Ala Cys His Ala
        195                 200                 205

Lys Thr Val Arg Val Asp Leu Ala Gly Ser Thr Asn Ser Ala Phe Val
    210                 215                 220

Arg Phe Asp Ile Lys Arg Arg Glu Val Leu Thr Ala Lys Val Ser Thr
225                 230                 235                 240

Pro Leu Ile Asp Glu Ile Asp Pro Ile Val Pro Leu Asp Asp Lys Glu
                245                 250                 255

Ser Ala Thr Val Thr Gly Leu Asp Leu Pro Asp Ile Asp Asp Ile Pro
            260                 265                 270

Thr Ala Thr Glu Pro Ala Ile Pro Lys Gln Ala Ala Ser Ser Asn
        275                 280                 285

Gly Arg Lys Pro Ala Thr Ala Ala Asp Asp Gly Asp Asp Ile Asn Gln
    290                 295                 300

Trp Ile
305

<210> SEQ ID NO 32
<211> LENGTH: 124
<212> TYPE: PRT
<213> ORGANISM: Actinoplanes sp. SE50/110

<400> SEQUENCE: 32

Met Ser Ile Phe Asp Leu Tyr Gly Gln Thr Gln His Leu Glu Arg Leu
1               5                   10                  15

Asp Pro Gln Gly Val Thr Asp Phe Val Asn Asp Glu Leu Ile Val Ser
            20                  25                  30

Asp Ile Asp Ser Arg Gln Ala Leu Glu Asp Leu Ala Trp Met Thr Ala
        35                  40                  45

Gly Leu Phe Ser Asp Gly Asn Gly Leu Ala Gln Leu Tyr Ile Asp Asp
    50                  55                  60

Gly Trp Asp Val Thr Asp Gly Ser His His Gly Leu Thr Glu Gln Gln
65                  70                  75                  80

Arg Gly Glu Leu Ile Ala Arg Leu Gly Thr Ile Ala His Asn Cys Gly
                85                  90                  95

Gln Leu Val Ala Glu Leu Cys Arg Arg Ala Ser Ala Val Lys Arg Glu
            100                 105                 110

Ser Gly Trp Asp Pro Leu Val Thr Thr Glu Pro Ile
        115                 120

<210> SEQ ID NO 33
<211> LENGTH: 293
<212> TYPE: PRT
<213> ORGANISM: Actinoplanes sp. SE50/110

<400> SEQUENCE: 33

Met Ser Thr Ile Ala Cys Asp Pro Leu Gly Thr Asp Arg Val Pro Val
1               5                   10                  15
```

```
Gly Pro Gly Met Ser Met Phe Asp Pro Leu Phe Ile Gly Ile Asp Glu
            20                  25                  30

Phe Gly Glu His Val Thr Leu Asp Ile Val Tyr His Asn Leu Leu Thr
        35                  40                  45

Ala Gly Glu Pro Gly Gly Lys Ser Gly Leu Leu Asn Leu Val Ala
50                  55                  60

Ala Thr Ala Ala Leu Ser Asp Asn Thr Arg Leu Ile Gly Met Asp Gly
65                  70                  75                  80

Lys Trp Val Glu Leu Gly Pro Trp Glu Pro Ile Met Asp Ala Phe Ile
                85                  90                  95

Gly Asp Asp Ile Asp Leu Ala Ile Lys Thr Val Arg Arg Leu Leu Thr
            100                 105                 110

Val Ala Arg Asn Arg Tyr Arg Trp Leu Leu Ala Asn Arg Arg Arg Lys
        115                 120                 125

Ile Thr Arg Glu Asp Asn Leu Ser Thr Ile Thr Ile Ile Asp Glu
130                 135                 140

Ile Ala Met Phe Ser Thr Val Leu Gly Thr Lys Ala Gln Gln Glu Glu
145                 150                 155                 160

Phe Ser Thr Leu Leu Arg Gly Leu Val Ala Leu Gly Arg Ala Cys Ala
                165                 170                 175

Met Pro Val Val Gly Ala Thr Gln Arg Pro Ser Trp Asp Ile Ile Pro
            180                 185                 190

Ala Ser Leu Arg Asp Leu Phe Gly Tyr Arg Cys Ala Phe Arg Cys Thr
        195                 200                 205

Thr Val Gly Ser Ser Asp Val Ile Leu Gly Ser Gly Leu Ala Glu Val
    210                 215                 220

Gly Phe Asp Ala Ser Thr Ile Ser Pro Asp Asn Pro Gly Glu Ala Leu
225                 230                 235                 240

Leu Arg Ala Glu Lys Lys Leu Pro Tyr Pro Ile Lys Ala Ala Trp Leu
                245                 250                 255

Ser Asp Asp Asp Ile Tyr Ala Ile Ala Asp Tyr Ala Ala Trp Leu Arg
            260                 265                 270

Arg Pro Thr Asn Pro Ala Thr Thr Thr Ser Tyr Thr Gly Arg Thr Gln
        275                 280                 285

Trp Glu Met Ala Ala
    290

<210> SEQ ID NO 34
<211> LENGTH: 66
<212> TYPE: PRT
<213> ORGANISM: Actinoplanes sp. SE50/110

<400> SEQUENCE: 34

Met Thr Glu Thr Arg Ala Gln Ala Ile Thr Gly Val Ile Ala Gly Thr
1               5                   10                  15

Ala Thr Thr Thr Ala Tyr Leu Ala Gly Leu Leu Val Gly His Leu Thr
            20                  25                  30

Arg His Gln Ala Pro Val Gly Val Leu Ala Leu Ala Ile Thr Ala Ala
        35                  40                  45

His Val Arg Lys His His Pro Arg Arg Trp Thr Ala Pro Gly Thr Thr
    50                  55                  60

Thr Ala
65
```

<210> SEQ ID NO 35
<211> LENGTH: 149
<212> TYPE: PRT
<213> ORGANISM: Actinoplanes sp. SE50/110

<400> SEQUENCE: 35

```
Met Lys Pro Thr His Gln Pro Ala Asn Thr Pro Val Thr Asp Pro Thr
1               5                   10                  15

Met Thr Pro Ala Ala Leu Leu Arg Ala Ala Leu Tyr Leu Gln Gln
            20                  25                  30

His Gly Trp Thr Gln His Gln Phe Tyr Asp Leu Val Ala Ile Thr Asp
        35                  40                  45

Gly Gln Phe Pro Pro Ala Cys Ala Ser Gly Ala Ile Met Thr Ala Ala
    50                  55                  60

Thr Gly Arg Cys Leu Ala Ser Gly Val Cys Thr Leu Asp Gly Asp Pro
65                  70                  75                  80

Asp Thr Ile Ala Ala Ile Arg Ala Leu Arg Val Phe Ala Ala Trp Leu
                85                  90                  95

Asp Leu Glu Tyr Thr Pro Thr Gly Phe Tyr Glu Thr Ser Ala Ile Asp
            100                 105                 110

Val Val Gly Asp Trp Asn Asp Tyr Glu Gly Arg Thr Arg Asp Glu Val
        115                 120                 125

Ile Glu Thr Leu Thr Asp Ala Ala Asp Asp Trp Asp Arg Leu His His
    130                 135                 140

Thr Gly Gly Ala Arg
145
```

<210> SEQ ID NO 36
<211> LENGTH: 108
<212> TYPE: PRT
<213> ORGANISM: Actinoplanes sp. SE50/110

<400> SEQUENCE: 36

```
Met Ser Leu Ser Tyr Val Asn Pro Ala Leu Thr Pro Thr Ala Pro Ala
1               5                   10                  15

Gly Asp Ser Arg Pro Ser Lys Pro Arg Arg Arg Asp Val Val Glu Asn
            20                  25                  30

Asp Glu Tyr Ala Ala Phe Val Arg Ile Ile Arg Ala Phe Ala Lys
        35                  40                  45

Arg Val Ala Thr Gly Asp Val Glu Ala Leu Arg Asp Met Val Gly Leu
    50                  55                  60

Ser Ala Gln Leu Asp Asp Ala Ile Ser Glu Ala Val Ile Gly Leu Arg
65                  70                  75                  80

Ala Tyr Gly Tyr Ser Trp Ala Glu Ile Gly Asp Arg Leu Gly Ile Ser
                85                  90                  95

Arg Gln Ala Ala Gln Gln Arg Trp Gly Gly Asp Lys
            100                 105
```

<210> SEQ ID NO 37
<211> LENGTH: 138
<212> TYPE: PRT
<213> ORGANISM: Actinoplanes sp. SE50/110

<400> SEQUENCE: 37

```
Met Thr Thr Ser Ala Leu Thr Asn Asp Tyr Leu Glu Ala Leu Gly Ala
1               5                   10                  15

Arg Thr Gly Ile Arg Val Glu Phe Tyr Asp Pro Thr Gly Ser Arg Tyr
            20                  25                  30
```

Gly Phe Pro Thr Phe Pro Tyr Arg Gln Ala Pro Glu His Leu Ala Thr
        35                  40                  45

Arg Arg Gln Leu Arg Ala Asp Gly Leu Cys Pro Asn Gly Tyr Asp Pro
 50                  55                  60

Val Ala Gln Ile Leu Trp Met His Arg Gly Gln Arg Val Ala Tyr
 65                  70                  75                  80

Leu Tyr Arg Arg Asp Leu Ala Lys Pro Lys Arg Val Pro Thr Ala Ala
                 85                  90                  95

Gln Leu Ala Val Val Ala Lys Met Leu Leu Ala Arg Arg Thr Cys Asp
                100                 105                 110

Ser Cys Gly Val Thr Arg Asp Tyr Tyr Ile Pro Arg Arg Thr Gly Ile
                115                 120                 125

Cys Leu Ser Cys Glu Val Gly Gly Ser Arg
            130                 135

<210> SEQ ID NO 38
<211> LENGTH: 61
<212> TYPE: PRT
<213> ORGANISM: Actinoplanes sp. SE50/110

<400> SEQUENCE: 38

Met Thr Thr Asp Pro Glu Asn Asn Ser Pro Ala Thr Thr Arg Cys Gln
 1               5                  10                  15

Cys Gly Asp His Tyr Cys Ala Glu Val Met Pro Lys Asp Gln Asp Arg
                20                  25                  30

Ser Gln Cys Cys Gln Tyr Cys Gly Tyr Arg Asp Cys Asp Val Cys Gly
            35                  40                  45

Trp Thr Asp Gln Ala Leu Arg Ser Pro Glu Val Ser Arg
 50                  55                  60

<210> SEQ ID NO 39
<211> LENGTH: 96
<212> TYPE: PRT
<213> ORGANISM: Actinoplanes sp. SE50/110

<400> SEQUENCE: 39

Met Ser Leu Ile Asp Leu Gly Lys His Leu Ala Thr Asp Asn Cys Leu
 1               5                  10                  15

Trp Cys Ile Gly Gly Met Ser Pro Ala Gly Ile His Pro Asp Leu Gly
                20                  25                  30

Pro Val Leu Cys Leu Cys Pro Thr Glu Gln Trp Cys Asp Glu Cys Gly
            35                  40                  45

Ser Thr Ser Leu Phe Pro Ala Glu Tyr Glu Thr Leu Asp Asp Arg Ile
 50                  55                  60

Asn Glu Leu Phe Asp Asp Gly Leu Ser Ala Val Trp Cys Glu Ala Cys
 65                  70                  75                  80

Met Gly Val Val Ala Val Ile Pro Val Thr Asn Asp Gly Gly Ile Arg
                85                  90                  95

<210> SEQ ID NO 40
<211> LENGTH: 169
<212> TYPE: PRT
<213> ORGANISM: Actinoplanes sp. SE50/110

<400> SEQUENCE: 40

Met Asn Pro Leu Arg Arg Lys Ala Ala Gln Gln Pro Thr Thr Gly Pro
 1               5                  10                  15

```
Ala Ala Pro Ala Ser Val Asn Leu Thr Glu Gln Phe Ala Ile Glu Tyr
            20                  25                  30

Ala Lys Ser Ala Val Pro Asn Met Leu Lys Ala Ile Asp Ser Val Lys
        35                  40                  45

Arg Tyr Asn Arg Ala Thr Leu Ile Gly Ala Leu Ile Thr Ser Tyr Leu
    50                  55                  60

His Gln Ala His Tyr Leu Ala Ser Thr Gly Ala Gly Tyr Phe Ala Tyr
65                  70                  75                  80

Leu Pro Pro Ala Ile Phe Asp Thr Ala Met Val Ser Met Leu Ile Val
                85                  90                  95

Val Arg Thr Pro Gly Ile Val Lys Asp Ala Lys Arg Trp Ala Met Ala
            100                 105                 110

Val Phe Ile Gly Ala Ala Leu Leu Ser Ala Thr Val Asn Phe Ala Ala
        115                 120                 125

Pro Ala Thr Ser Ala Cys Ala Ser Ser Ser Pro Trp Ser Ser Ser Trp
    130                 135                 140

Ser Ser Ala Ser Asn Ser Ser Pro Asp Ala Ser Ala Pro Thr Ser Pro
145                 150                 155                 160

Pro Ser Thr Asn Lys Pro Pro Asn Ser
                165

<210> SEQ ID NO 41
<211> LENGTH: 107
<212> TYPE: PRT
<213> ORGANISM: Actinoplanes sp. SE50/110

<400> SEQUENCE: 41

Met Thr Ala Val Asn Lys Ile Lys Ala Arg Gly Thr Ala Thr Thr Pro
1               5                   10                  15

Glu Pro Glu His Thr Thr Thr Gly Pro Thr Ala Pro Val Glu Gln Pro
            20                  25                  30

Ala Thr Pro Gln Thr Ala Pro Val Val Pro Ala His Leu Leu Pro Ala
        35                  40                  45

Ala Arg Phe Ser Val Val Gln His Glu Gln Thr Thr Gly Gln Pro Ile
    50                  55                  60

Thr Ala Asp Asp Leu Ala Leu Arg Leu Asn Ile Thr Pro Ala Val Ala
65                  70                  75                  80

Glu Thr Leu Ile Thr Thr Ile Arg Asp Thr Asn Pro Ala Arg Ile Asn
                85                  90                  95

Gly His Ile Pro Thr Leu Thr Gly Gly Ala Arg
            100                 105

<210> SEQ ID NO 42
<211> LENGTH: 97
<212> TYPE: PRT
<213> ORGANISM: Actinoplanes sp. SE50/110

<400> SEQUENCE: 42

Met Thr Phe Val His Val Asp Ile His His Ile Thr His Thr Cys Pro
1               5                   10                  15

Ala Asn Pro Glu Leu His Pro Phe Asp Thr Arg Arg Thr Ile Val Ala
            20                  25                  30

Thr Val Asp Gly Gly Pro Cys Arg Asn Pro Ile Ser Ile Arg Cys Gly
        35                  40                  45

Asp Lys Thr Ala Val Ile Asp Cys Gly Arg His Glu Pro His His Arg
    50                  55                  60
```

Gln Cys Pro Ala Cys Arg Ile Thr Val Ile Glu Arg His Ile Thr Ser
65                  70                  75                  80

Thr Phe Val Gly His His Gly Pro Gln Leu Ala Thr Thr Arg Ile Ala
                85                  90                  95

Ala

<210> SEQ ID NO 43
<211> LENGTH: 598
<212> TYPE: PRT
<213> ORGANISM: Actinoplanes sp. SE50/110

<400> SEQUENCE: 43

Met Ser Thr Ser Thr Leu Asp Leu Ala Pro Arg Glu Asn Ser Ala Arg
1               5                   10                  15

Gly Ala Gly Ser Asn Ala Asp Ala Trp Thr Pro Pro Ala Asp Tyr
            20                  25                  30

Thr Ala Ala Gly Gln Ala Leu Thr Arg Ala Thr Gln Pro Gly Tyr Phe
            35                  40                  45

Asp Trp Leu Asp His Val Arg Ala Ala Gly Cys Thr Arg Pro Val
        50                  55                  60

Arg Leu Thr Gly Thr Leu Asp Thr Ile Glu Ala Thr Thr Gly Arg Leu
65                  70                  75                  80

Leu Asp Ser Arg His Thr Asp Gln Leu Pro Asp Ala Ala Ile Tyr Lys
                85                  90                  95

Ala Cys Gly Asn Arg Arg Ser Thr Val Cys Pro Ala Cys Ala Arg Thr
            100                 105                 110

Tyr Gln Arg Asp Ala Phe Gln Ile Leu Arg Ala Gly Leu Ile Gly Gly
            115                 120                 125

Lys Gly Val Pro Thr Thr Val Ala Arg His Pro Ala Val Phe Val Thr
130                 135                 140

Leu Thr Ala Pro Ser Phe Gly Ala Val His Thr Arg His Val Arg Lys
145                 150                 155                 160

His Thr Cys Thr Asn Arg Ala Arg Cys Ser Cys Arg Pro Glu Pro Cys
                165                 170                 175

His Ala Arg Arg Asn Pro Gly Leu Cys Gln His Tyr Gln Pro Ala Val
            180                 185                 190

Cys Trp Ala Arg His Glu Pro Gly Asp Pro Gln Leu Gly Arg Pro Leu
            195                 200                 205

Cys Leu Asp Cys Tyr Asp His Gln His His Val Val Trp Asn Leu Phe
210                 215                 220

Ser Gly Glu Leu Trp His Arg Thr Lys Gln Asp Ala Glu Arg Arg Leu
225                 230                 235                 240

Ala Lys Leu Cys Lys Ala Arg Gly Ile Pro Phe His Glu Val Ser Asn
            245                 250                 255

Gly Lys Asn Leu Arg Arg Ile Pro Pro Val Arg Leu Ala His Gly Lys
            260                 265                 270

Ala Ala Glu Met Gln Arg Arg Gly Ala Val His Phe His Ala Leu Ile
            275                 280                 285

Arg Leu Asp Gly Ile Asp Pro Thr Asp Pro Thr Arg Val Val Ala Pro
290                 295                 300

Pro Pro Gly Ile Gly Leu Asn Asp Leu Val Asp Ala Leu Thr Ala Ala
305                 310                 315                 320

Ser Asp Ile Asp Phe Thr Thr Pro Asp His Pro Asp Arg Pro Asp Gly
                325                 330                 335

-continued

Trp Pro Met Ala Trp Gly Glu Gln Ile Asp Ile Arg Pro Ile Ser Leu
            340                 345                 350

Thr Gly Thr Gly Glu Val Thr Asp Ser Met Val Ala Gly Tyr Leu Ala
        355                 360                 365

Lys Tyr Ala Thr Lys Ser Thr Glu Ile Thr Gly His Asn Ser Thr Arg
    370                 375                 380

Ile Thr Gly Asp Thr Ile Thr Gln His Ala Asp Pro Ala Gly Asp His
385                 390                 395                 400

Ile Ala Arg Leu Ile His Ala Cys Trp His Leu Gly Asn Asp Pro Asp
                405                 410                 415

Ala Pro Ala Gly Lys Thr Ala Ile Arg Leu Pro Val Tyr Thr Gly Thr
            420                 425                 430

Ala Gly Ala Lys Ile Arg Gln Pro Phe Gly Ala Pro Arg His Cys Pro
        435                 440                 445

Asp Cys Gly Thr Arg Thr Arg Tyr Arg Thr Cys Pro Val Cys Val Ala
    450                 455                 460

Glu Arg Gln Ala Ser Leu Asp Thr Gln Arg Pro Asn Asp Arg Gln Pro
465                 470                 475                 480

Thr Pro Tyr Ala Arg Leu Arg Arg Trp Ala His Met Leu Gly Phe Gly
                485                 490                 495

Gly His Phe Leu Thr Lys Ala Arg Arg Tyr Ser Val Thr Phe Arg Leu
            500                 505                 510

Leu Arg Glu Thr Arg Ile Asp Phe Arg Arg Ala Glu Pro Asp Pro Ala
        515                 520                 525

Asp Asn Ala Thr Val His Thr Val Asp His Leu Asp Glu Thr Thr Leu
    530                 535                 540

Ile Val Gly Thr Leu Thr Phe Ala Gly Val Gly Trp His Thr Thr Gly
545                 550                 555                 560

Asp Ala Leu Leu Ala Asn Thr Ala Ala Gln Ala Arg Glu Arg Gln
                565                 570                 575

Ala Ile Gly Arg Glu Glu Leu Ala His Glu Ala Ser Thr Ser Arg Pro
            580                 585                 590

Val Ala Leu Asn Ala Ala
        595

<210> SEQ ID NO 44
<211> LENGTH: 68
<212> TYPE: PRT
<213> ORGANISM: Actinoplanes sp. SE50/110

<400> SEQUENCE: 44

Met Asp Gly Ile Thr Pro Lys Ala Leu Tyr Arg Ile Pro Glu Ala Met
1               5                   10                  15

Arg Met Leu Ser Leu Ser Arg Ser Val Ile Tyr Glu Leu Ile Arg Ser
            20                  25                  30

Gly Arg Leu Arg Thr Val Lys Glu Gly Arg Thr Arg Leu Val Pro Ala
        35                  40                  45

Ser Ala Ile Thr Ala Tyr Val Thr Leu Leu Glu Gln Glu Ser Lys Lys
    50                  55                  60

Gly Val Ala Ala
65

<210> SEQ ID NO 45
<211> LENGTH: 388
<212> TYPE: PRT
<213> ORGANISM: Actinoplanes sp. SE50/110

<400> SEQUENCE: 45

```
Met Thr Lys Arg Arg Ser Arg Gly Asp Gly Leu His Trp Asp Glu
1               5                   10                  15

Gln Arg Gln Arg Trp Ile Ala Ser Val Thr Val Gly Tyr Thr Pro Ala
        20                  25                  30

Gly Lys Arg Ile Val Arg Lys Ala Ser Gly Lys Thr Lys Thr Glu Ala
            35                  40                  45

Asn Asn Ala Leu Arg Gln Lys Ile Arg Glu Tyr Gln Asp Gly Leu Ser
        50                  55                  60

Ile Pro Thr Thr Gly Tyr Thr Val Ala Asp Val Thr Asp Trp Leu
65                  70                  75                  80

Thr Tyr Gly Leu Pro Asp Val Asp Glu Glu Thr Val Asn Asn Tyr Thr
                85                  90                  95

Leu Leu Ala Asn Gly His Ile Ile Pro Ala Ile Gly Ala Arg Lys Leu
            100                 105                 110

Arg Asp Pro Ser Lys Gln Lys Glu Leu Ser Ala Thr Asp Ile Asp Arg
        115                 120                 125

Trp Leu Ala Asp Lys Ala Lys Ile Leu Ser Thr Arg Thr Leu Arg Leu
130                 135                 140

Leu His Ser Ile Ala Asn Arg Ala Ile Asn Arg Ala Met Ala Arg Asp
145                 150                 155                 160

Lys Val Met Arg Asn Val Val Ala Leu Cys Lys Val Pro Thr Gly Thr
                165                 170                 175

Ala Gly Arg Pro Ser Lys Ser Leu Thr Tyr Glu Gln Ala Lys Ala Leu
            180                 185                 190

Leu Val Ala Ala Glu Ser Ser Leu His Ala Tyr Val Val Leu Ser
        195                 200                 205

Leu Leu Thr Gly Ala Arg Thr Glu Glu Leu Arg Glu Leu Thr Trp Gln
210                 215                 220

His Val Asp Leu Val Gly Arg Pro Asp Ala Glu Pro Pro Ile Pro Pro
225                 230                 235                 240

Ala Ile His Val Trp His Ser Val Arg Ala His Gly Asp Thr Lys Thr
                245                 250                 255

Lys Lys Ser Arg Arg Ser Leu Ala Leu Pro Val Arg Cys Val Arg Val
            260                 265                 270

Leu Thr Ala Gln Arg Ala Ala His Gly Asp Pro Arg Pro Asp Asp Tyr
        275                 280                 285

Val Cys Ala Ser Lys Val Gly Thr Gln Leu Asp Arg His Asn Val Leu
290                 295                 300

Arg Ala Phe Arg Ala Ile Val Ala Ala Val Pro Gly Met Asn Pro Ala
305                 310                 315                 320

Glu Trp Thr Pro Arg Glu Leu Arg His Ser Phe Val Ser Leu Leu Ser
                325                 330                 335

Asp Asn Gly Met Ser Ile Glu Gly Ile Ala Asp Leu Cys Gly His Ser
            340                 345                 350

Gly Thr Ser Ile Thr Glu Thr Val Tyr Arg His Gln Leu Arg Pro Val
        355                 360                 365

Leu Leu Asn Gly Ala Val Ala Met Asp Arg Ile Phe Gly Pro Asp Asp
370                 375                 380

Thr Pro Gly Ala
385
```

```
<210> SEQ ID NO 46
<211> LENGTH: 21
<212> TYPE: DNA
<213> ORGANISM: Actinoplanes sp. SE50/110
<220> FEATURE:
<221> NAME/KEY: allele
<222> LOCATION: (15)
<223> OTHER INFORMATION: t or c
<220> FEATURE:
<221> NAME/KEY: allele
<222> LOCATION: (18)
<223> OTHER INFORMATION: c or t

<400> SEQUENCE: 46
gtcacccagt tagtnacnca g                                              21
```

ACTINOMYCETE INTEGRATIVE AND CONJUGATIVE ELEMENT FROM *ACTINOPLANES* SP. SE50/110 AS PLASMID FOR GENETIC TRANSFORMATION OF RELATED ACTINOBACTERIA

The present application includes a Sequence Listing filed herewith using EFS-web. The Sequence Listing is presented in a single file named BHC111053-PCT-US01-Seq-Listing.txt, last modified Jan. 5, 2016, and having 74,613 bytes, the disclosure of which is incorporated herein by reference in its entirety.

BACKGROUND OF THE INVENTION

The prokaryotic organism *Actinoplanes* sp. SE50/110 produces the alpha-glucosidase inhibitor acarbose, which is used worldwide in the treatment of diabetes mellitus type-2. Based on the fact, that the incidence of diabetes type-2 is rapidly rising worldwide, an increasing demand for acarbose is expected in the future. In order to meet these expectations, genetic manipulations of the strain and its derivatives have to be carried out, aiming at increasing acarbose yields. However, currently no tools for genetic manipulation exist for this strain, hampering the process of strain improvement.

BRIEF SUMMARY OF THE INVENTION

The present invention is directed to an innate DNA sequence within the complete genome sequence of *Actinoplanes* sp. SE50/110 which resembles the structure of an actinomycete integrative and conjugative element (AICE). Related AICEs were used for establishing genetic manipulation tools for other bacteria in the past. In this document, we describe the unique features of the specific AICE found in *Actinoplanes* sp. SE50/110, which are clearly distinct from any other known AICE as a whole, but share minor parts with varying sequence similarity with other characterized AICEs from other species.

DETAILED DESCRIPTION OF THE INVENTION

*Actinoplanes* sp. SE50/110 is a Gram-positive, aerobic bacterium with a high G+C content genome of about 9.25 MB in size (Schwientek et al., 2012). The medically important organism is the natural producer of a variety of chemically related substances, which were found to inhibit human alpha-glucosidases (Caspary and Graf, 1979), making them especially suitable for pharmaceutical applications (Frommer et al., 1975, 1977 a, 1977 b, 1979). In particular, the pseudotetrasaccharide acarbose, which is synthesized through enzymes encoded in the well characterized acarbose gene cluster (Wehmeier and Piepersberg, 2004), is used worldwide in the treatment of type-2 diabetes mellitus (non-insulin-dependent).

Diabetes mellitus type-2 is a chronic disease with more than 250 million people affected worldwide. Inappropriately managed or untreated, it can lead to severe cases of renal failure, blindness, slowly healing wounds and arterial diseases, including coronary artery atherosclerosis (IDF, 2009). As the incidence of diabetes type 2 is rapidly rising worldwide, an ever increasing demand for diabetes drugs like acarbose needs to be anticipated. The pseudotetrasaccharide acarbose is currently produced by industrial fermentation of yield-optimized strains, which are based on the wild-type bacterium *Actinoplanes* sp. SE50/110 (ATCC 31044; CBS 674.73). While classical strain optimization through conventional mutagenesis was a very successful way of increasing the production of acarbose in the past, this strategy seems to have reached its limits by now. In order to further increase production efficacy, targeted genetic engineering methods have to be applied, which requires a functional transformation system for *Actinoplanes* sp. SE50/110. Previous experiments revealed that *Actinoplanes* sp. SE50/110 and *Actinoplanes friuliensis* (and presumably most other *Actinoplanes* spp.) do not allow for standard transformation methods like electroporation or PEG-mediated transformation, despite serious efforts have been made (Heinzelmann et al., 2003). In this context, an actinomycete integrative and conjugative element (AICE) has been identified on the *Actinoplanes* sp. SE50/110 genome (GenBank:CP003170), which can be used for this purpose as has been shown previously for related species (Hosted et al., 2005).

Figure 1:
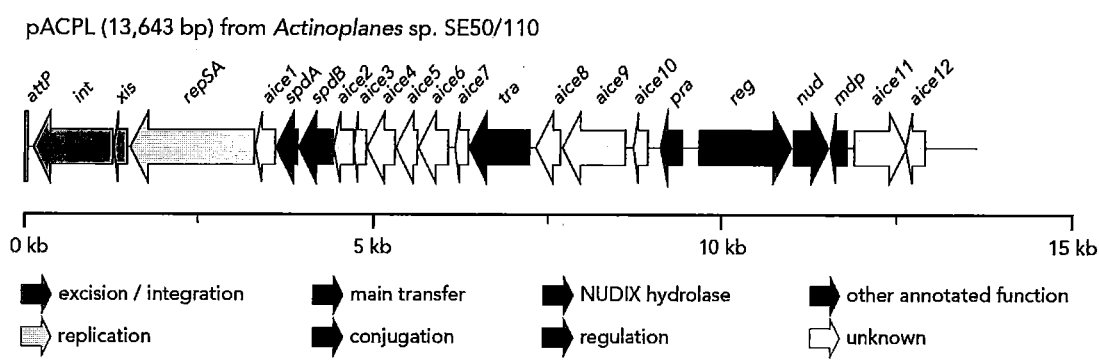
FIG. 1 presents the structural organization of the newly identified actinomycete integrative and conjugative element (AICE) pACPL from *Actinoplanes* sp. SE50/110. Typical genes that are also found on other AICEs are colored: excision/integration (orange), replication (yellow), main transfer (dark blue), conjugation (blue), NUDIX hydrolase (dark green), regulation (green), other annotated function (red), unknown function (gray).

AICEs are a class of mobile genetic elements possessing a highly conserved structural organization with functional modules for excision/integration, replication, conjugative transfer and regulation (te Poele, Bolhuis, et al., 2008). Being able to replicate autonomously, they are also said to mediate the acquisition of additional modules encoding functions, such as resistance and metabolic traits, which confer a selective advantage to the host under certain environmental conditions (Burrus and Waldor, 2004). A new AICE, designated pACPL, was identified in the complete genome sequence of *Actinoplanes* sp. SE50/110 (FIG. 1). Its size of 13.6 kb and the structural gene organization are in good accordance with other known AICEs of closely related species like *Micromonospora rosario, Salinispora tropica* or *Streptomyces coelicolor* (te Poele, Bolhuis, et al., 2008).

Most known AICEs subsist in their host genome by integration in the 3' end of a tRNA gene by site-specific recombination between two short identical sequences (att identity segments) within the attachment sites located on the genome (attB) and the AICE (attP), respectively (te Poele, Bolhuis, et al., 2008). In pACPL, the att identity segments are 43 nt in size and attB overlaps the 3' end of a proline tRNA gene. Moreover, the identity segment in attP is flanked by two 21 nt repeats containing two mismatches: GTCAC-CCAGTTAGT(T/C)AC(C/T)CAG (SEQ ID NO: 46). These exhibit high similarities to the arm-type sites identified in the AICE pSAM2 from *Strepomyces ambofaciens*. For pSAM2 it was shown that the integrase binds to these repeats and that they are essential for efficient recombination (Raynal et al., 2002).

Figure 2:
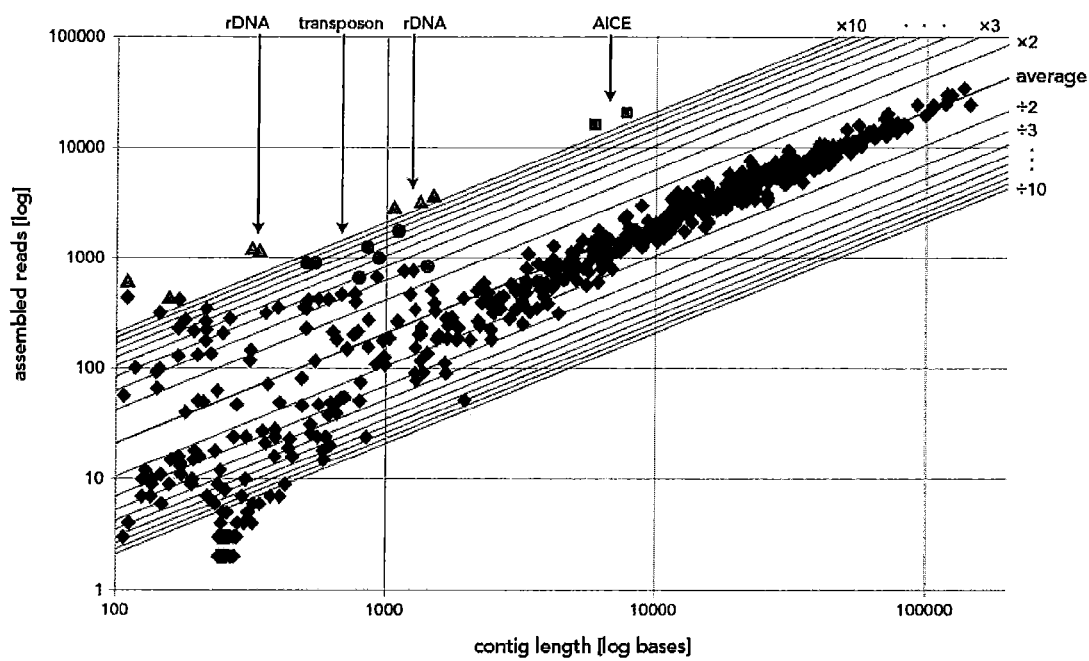
FIG. 2 shows a scatter plot of 571 *Actinoplanes* sp. SE50/110 contigs resulting from automatic combined assembly of paired end and whole genome shotgun pyrosequencing runs. The average number of reads per base is 21.12 and is depicted in the plot by the central diagonal line marked with "average". Additional lines indicate the factor of over- and underrepresentation of reads per base up to a factor of 10 and 1/10 fold, respectively. The axes represent logarithmic scales. Large and highly overrepresented contigs are highlighted by special symbols. Each contig is represented by one of the following symbols: diamond, regular contig; square, contig related to the actinomycete integrative and conjugative element (AICE); triangle, contig related to ribosomal operon (rrn); circle, related to transposons.

Besides the proline tRNA genomic integration site, pACPL was shown to subsist in at least twelve copies (FIG. 2) as an extrachromosomal element in an average *Actinoplanes* sp. SE50/110 cell (Schwientek et al., 2012). pACPL hosts 22 protein coding sequences.

The actinomycete integrative and conjugative element of the present invention is selected from the group consisting of:
  a) a polynucleotide having the sequence of SEQ ID NO: 1,
  b) a polynucleotide which hybridizes under stringent conditions to a polynucleotide as specified in (a) and
  c) a polynucleotide having at least 90% identity with the sequence of SEQ ID NO: 1.

Preferred are AICEs having at least 95% identity with the sequence of SEQ ID NO: 1. More preferred are AICEs having at least 98% identity with the sequence of SEQ ID NO: 1. The present invention is further related to a host cell that has been transformed with the actinomycete integrative and conjugative element described above. The most preferred host cell is an *Actinoplanes* sp. The host cell is useful in a method for preparation of biological products comprising the steps of
  a) culturing the above host cell in a useful medium,
  b) harvesting the product from the culture and
  c) isolating and purifying the product.

The most preferred product in this method is acarbose.

Detailed description of the 22 protein coding sequences of pACPL

The gene int (genomic locus tag: ACPL 6310) encodes the integrase of the AICE with a length of 388 amino acids. Its sequence shows 74% similarity to an integrase (GenBank: EFL40120.1) of *Streptomyces griseoflavus* Tu4000 within the first 383 amino acids. The integrase domain of the protein is located from amino acid 182-365 and shows high similarity (e-value 2.90e-21) to the Int/Topo IB signature motif (conserved domain: cd01182). The integrase is responsible for integration into a tRNA gene by site-specific recombination which occurs between the two similar attachment sites attB on the chromosome and attP on the AICE (te Poele, Bolhuis, et al., 2008).

The gene xis (genomic locus tag: ACPL 6309) encodes the excisionase of the AICE with a length of 68 amino acids). It shows highest similarity to the hypothetical protein Sros 7036 (GenBank: ACZ89735.1) from *Streptosporangium roseum* DSM 43021. The protein contains a moderately conserved (e-value: 1.31e-07) helix-turn-helix motif (pfam12728) between amino acids 9-55. Xis is needed in combination with Int to mediate the excision of the AICE from the chromosome in preparation for amplification and transfer to other hosts (te Poele, Bolhuis, et al., 2008).

The gene repSA (genomic locus tag: ACPL 6308) encodes the replication initiation protein of the AICE with a length of 598 amino acids. It has highest similarity to a putative plasmid replication initiation protein (GenBank: ADL48867.1) from *Micromonospora aurantiaca* ATCC 27029. The protein resembles the well characterized RepSA protein from *Streptomyces ambofaciens* which has been found to apply a rolling cycle replication mechanism (Hagege et al., 1993).

The gene aice1 (genomic locus tag: ACPL 6307) encodes a protein with unknown function with a length of 97 amino acids. It shows 69% similarity in the first 80 amino acids to the hypothetical protein Micau 5360 (GenBank: ADL48866.1) from *Micromonospora aurantiaca* ATCC 27029.

The gene spdA (genomic locus tag: ACPL 6306) encodes a putative spread protein of the AICE with a length of 107 amino acids. SpdA shows 54% similarity to a spread protein (GenBank: ABD10289.1) from *Frankia* sp. CcI3. Spread proteins are involved in pock formation, which reflects a temporary growth delay of recipient cells that are in the process of acquiring an AICE from a donor cell. Thus, spread proteins assist in the intramycelial spread of (Kataoka et al., 1994; Grohmann et al., 2003; te Poele, Bolhuis, et al., 2008).

The gene spdB (genomic locus tag: ACPL 6305) encodes a putative spread protein of the AICE with a length of 169 amino acids. SpdB shows 84% similarity between the amino acids 40-131 to a spread protein (GenBank: AAX38998.1) from *Micromonospora rosaria*. Spread proteins are involved in pock formation, which reflects a temporary growth delay of recipient cells that are in the process of acquiring an AICE from a donor cell. Thus, spread proteins assist in the intramycelial spread of (Kataoka et al., 1994; Grohmann et al., 2003; te Poele, Bolhuis, et al., 2008). A signal peptide has been found for SpdB, its cleavage site is predicted at position 18. Furthermore, three transmembrane helices were found at positions i53-70o75-97i109-131o.

The gene aice2 (genomic locus tag: ACPL 6304) encodes a protein with unknown function with a length of 96 amino acids. It shows 57% similarity between the amino acids 12-89 to the hypothetical protein Micau 5358 (GenBank: ADL48864.1) from *Micromonospora aurantiaca* ATCC 27029.

The gene aice3 (genomic locus tag: ACPL 6303) encodes a protein with unknown function with a length of 61 amino acids. It shows no significant similarity to any of the proteins in public databases.

The gene aice4 (genomic locus tag: ACPL 6302) encodes a protein with unknown function with a length of 138 amino acids. It shows 69% similarity in the last 113 amino acids to the hypothetical protein Micau 5357 (GenBank: ADL48863.1) from *Micromonospora aurantiaca* ATCC 27029.

The gene aice5 (genomic locus tag: ACPL 6301) encodes a protein with unknown function with a length of 108 amino acids. It shows 79% similarity to the complete amino acid sequence of the hypothetical protein Micau 5356 (GenBank: ADL48862.1) from *Micromonospora aurantiaca* ATCC 27029. This protein has a low pfam hit (e-value 0.0022) to sigma factors with extracytoplasmic function (ECF). These sigma factors can bind to RNA polymerase in order to stimulate the transcription of specific genes. They are believed to be activated upon receiving a stimulus from the environment and are often cotranscribed with one or more negative regulators (Helmann, 2002).

The gene aice6 (genomic locus tag: ACPL 6300) encodes a protein with unknown function with a length of 149 amino acids. It shows 50% similarity to the complete amino acid sequence of the hypothetical protein VAB18032_01645 (GenBank: AEB47413.1) from *Verrucosispora maxis* AB-18-032.

The gene aice7 (genomic locus tag: ACPL 6299) encodes a protein with unknown function with a length of 66 amino acids. It shows no similarity to any of the proteins in public databases. Aice7 contains a single transmembrane helix ranging from amino acid 9-31.

The gene tra (genomic locus tag: ACPL_6298) encodes the main transfer protein of the AICE with a length of 293 amino acids. It exhibits 74% similarity throughout the major part to a cell division protein (GenBank: ADL48859.1) from *Micromonospora aurantiaca* ATCC 27029. Tra contains a domain with significant similarity (e-value 3.1e-14) to the FtsK/SpoIIIE domain between amino acids 29-187, which is found in all AICEs and *Streptomyces* transferase genes (te Poele, Bolhuis, et al., 2008). Several experiments have provided evidence, that homologues of Tra are responsible for the translocation of double-stranded DNA to the recipient strains. Translocation occurs at the hyphal tips of the mating mycelium (Possoz et al., 2001; Reuther et al., 2006).

The gene aice8 (genomic locus tag: ACPL 6297) encodes a protein with unknown function with a length of 124 amino acids. It shows 44% similarity between the amino acids 44-116 to the sequence of the FadE6 protein (GenBank: EGT86701.1) from Mycobacterium colombiense CECT 3035. While the complete FadE6 protein has 733 amino acids that resemble an acyl-CoA dehydrogenase, Aice8 is unlikely to have a similar function as it does not contain the catalytic domains of FadE6 and is only 124 amino acids in length.

The gene aice9 (genomic locus tag: ACPL 6296) encodes a protein with unknown function with a length of 320 amino acids. It shows 68% similarity throughout the major part of the sequence to the hypothetical protein Micau 5352 (GenBank: ADL48858.1) from *Micromonospora aurantiaca* ATCC 27029. This protein contains four transmembrane helices at positions i32-51o57-79i88-110o115-134i.

The gene aice10 (genomic locus tag: ACPL_6295) encodes a protein with unknown function with a length of 69 amino acids. It shows no significant similarity to any of the proteins in public databases.

The gene pra (genomic locus tag: ACPL_6294) is likely to encode the activator of the repSA, xis and int genes. It has a length of 105 amino acids and shows 90% similarity throughout the complete sequence to the hypothetical protein Micau 5352 (GenBank: ADL48857.1) from *Micromonospora aurantiaca* ATCC 27029. Pra, which regulates the transfer and replication of the AICE, is believed to be repressed by the transcriptional regulator KorSA in the AICE pSAM2 from *Streptomyces ambofaciens* (Sezonov et al., 2000). By repressing Pra, the AICE remains in its integrated from on the chromosome.

The gene reg (genomic locus tag: ACPL 6293) encodes a regulatory protein of the AICE with a length of 444 amino acids. It shows 50% similarity throughout the complete sequence to a putative regulator (GenBank: CCB75999.1) from *Streptomyces cattleya* NRRL 8057. Reg contains a helix-turn-helix domain, ranging from amino acids 4-72. Although the sequence similarity between Reg and KorSA from pSAM2 is very low, the localization of reg between the pra and nud genes may be an indication for Reg resembling a homologue to KorSA, which is frequently found in this genetic organization (te Poele, Bolhuis, et al., 2008).

The gene nud (genomic locus tag: ACPL 6292) encodes a protein which contains a NUDIX-hydrolase domain between amino acids 29-144. It has a size of 172 amino acids and shows 72% similarity throughout the sequence to a hypothetical protein (GenBank: EFL09132.1) of *Streptomyces* sp. AA4 and various NUDIX hydrolases from closely related species. Nud exhibits 42% similarity between amino acids 21-108 to the Pif protein of pSAM2. Pif also contains a NUDIX-hydrolase domain, and was shown to be involved in intercellular signaling, which is believed to inhibit replication and transfer of the AICE in order to prevent redundant transfer between pSAM2 harboring cells (Possoz et al., 2003; te Poele, Bolhuis, et al., 2008). It is therefore likely, that Pra, Reg and Nud in pACPL resemble a similar regulatory mechanism like Pra, KorSA and Pif do for pSAM2.

The gene mdp (genomic locus tag: ACPL 6291) encodes a metal-dependent phosphohydrolase with a length of 80 amino acids. It exhibits 66% similarity throughout its sequence to a metal-dependent phosphohydrolase (GenBank: ABD10513.1) from *Frankia* sp. CcI3. Mdp encoding genes are frequently found in a cluster with pra, reg and nud homologues on other AICEs (te Poele, Bolhuis, et al., 2008). Metal-dependent phosphohydrolases may be involved in signal transduction or nucleic acid metabolism (te Poele, Samborskyy, et al., 2008).

The gene aice11 (genomic locus tag: ACPL 6290) encodes a protein with unknown function with a length of 256 amino acids. It shows no significant similarity to any of the proteins in public databases.

The gene aice12 (genomic locus tag: ACPL 6289) encodes a protein with unknown function with a length of 93 amino acids. It shows no significant similarity to any of the proteins in public databases.

REFERENCES

Burrus, V., Waldor, M. K., 2004. Shaping bacterial genomes with integrative and conjugative elements. Res. Microbiol 155, 376-386.

Caspary, W. F., Graf, S., 1979. Inhibition of human intestinal alpha-glucosidehydrolases by a new complex oligosaccharide. Res Exp Med (Berl) 175, 1-6.

Frommer, W., Junge, B., Keup, U., Mueller, L., Schmidt, D., 1977. Amino sugar derivatives. German patent DE 2347782 (U.S. Pat. No. 4,062,950).

Frommer, W., Junge, B., Müller, L., Schmidt, D., Truscheit, E., 1979. Neue Enzyminhibitoren aus Mikroorganismen. Planta Med 35, 195-217.

Frommer, W., Puls, W., Schäfer, D., Schmidt, D., 1975. Glycoside-hydrolase enzyme inhibitors. German patent DE 2064092 (U.S. Pat. No. 3,876,766).

Frommer, W., Puls, W., Schmidt, D., 1977. Process for the production of a saccharase inhibitor. German patent DE 2209834 (U.S. Pat. No. 4,019,960).

Grohmann, E., Muth, G., Espinosa, M., 2003. Conjugative Plasmid Transfer in Gram-Positive Bacteria. Microbiol. Mol. Biol. Rev. 67, 277-301.

Hagège, J., Pernodet, J. L., Friedmann, A., Guérineau, M., 1993. Mode and origin of replication of pSAM2, a conjugative integrating element of *Streptomyces ambofaciens*. Mol. Microbiol. 10, 799-812.

Heinzelmann, E., Berger, S., Puk, O., Reichenstein, B., Wohlleben, W., Schwartz, D., 2003. A Glutamate Mutase Is Involved in the Biosynthesis of the Lipopeptide Antibiotic Friulimicin in *Actinoplanes friuliensis*. Antimicrob Agents Chemother 47, 447-457.

Helmann, J. D., 2002. The extracytoplasmic function (ECF) sigma factors. Adv. Microb. Physiol. 46, 47-110.

Hosted, T. J., Jr, Wang, T., Horan, A. C., 2005. Characterization of the *Micromonospora rosaria* pMR2 plasmid and development of a high G+C codon optimized integrase for site-specific integration. Plasmid 54, 249-258.

IDF, 2009. IDF Diabetes Atlas, 4th edn. International Diabetes Federation, Brussels, Belgium: International Diabetes Federation.

Kataoka, M., Kiyose, Y. M., Michisuji, Y., Horiguchi, T., Seki, T., Yoshida, T., 1994. Complete Nucleotide Sequence of the *Streptomyces nigrifaciens* Plasmid, pSN22: Genetic Organization and Correlation with Genetic Properties. Plasmid 32, 55-69.

te Poele, E. M., Bolhuis, H., Dijkhuizen, L., 2008. Actinomycete integrative and conjugative elements. Antonie Van Leeuwenhoek 94, 127-143.

te Poele, E. M., Samborskyy, M., Oliynyk, M., Leadlay, P. F., Bolhuis, H., Dijkhuizen, L., 2008. Actinomycete integrative and conjugative pMEA-like elements of Amycolatopsis and Saccharopolyspora decoded. Plasmid 59, 202-216.

Possoz, C., Gagnat, J., Sezonov, G., Guérineau, M., Pernodet, J.-L., 2003. Conjugal immunity of *Streptomyces* strains carrying the integrative element pSAM2 is due to the pif gene (pSAM2 immunity factor). Mol. Microbiol. 47, 1385-1393.

Possoz, C., Ribard, C., Gagnat, J., Pernodet, J. L., Guérineau, M., 2001. The integrative element pSAM2 from *Streptomyces*: kinetics and mode of conjugal transfer. Mol. Microbiol. 42, 159-166.

Raynal, A., Friedmann, A., Tuphile, K., Guerineau, M., Pernodet, J.-L., 2002. Characterization of the attP site of the integrative element pSAM2 from *Streptomyces ambofaciens*. Microbiology (Reading, Engl.) 148, 61-67.

Reuther, J., Gekeler, C., Tiffert, Y., Wohlleben, W., Muth, G., 2006. Unique conjugation mechanism in mycelial streptomycetes: a DNA-binding ATPase translocates unprocessed plasmid DNA at the hyphal tip. Mol. Microbiol. 61, 436-446.

Schwientek, P., Szczepanowski, R., Ruckert, C., Kalinowski, J., Klein, A., Selber, K., Wehmeier, U. F., Stoye, J., Paler, A., 2012. The complete genome sequence of the acarbose producer *Actinoplanes* sp. SE50/110. BMC Genomics 1-2.

Sezonov, G., Possoz, C., Friedmann, A., Pernodet, J. L., Guérineau, M., 2000. KorSA from the *Streptomyces* integrative element pSAM2 is a central transcriptional repressor: target genes and binding sites. J. Bacteriol. 182, 1243-1250.

Wehmeier, U. F., Piepersberg, W., 2004. Biotechnology and molecular biology of the alpha-glucosidase inhibitor acarbose. Appl. Microbiol. Biotechnol 63, 613-625.

The invention claimed is:

1. A method for preparation of biological products comprising the steps of
culturing a host cell transformed with an actinomycete integrative and conjugative element having the sequence of SEQ ID NO: 1, wherein the host cell is an *Actinoplanes* sp,
harvesting the product from the culture and isolating and purifying the product.

2. The method of claim 1 wherein the product is acarbose.